(12) United States Patent
Dai et al.

(10) Patent No.: US 8,735,562 B2
(45) Date of Patent: May 27, 2014

(54) ISOLATED FUNGAL PROMOTERS AND GENE TRANSCRIPTION TERMINATORS AND METHODS OF PROTEIN AND CHEMICAL PRODUCTION IN A FUNGUS

(75) Inventors: Ziyu Dai, Richland, WA (US); Linda L. Lasure, Fall City, WA (US); Jon K. Magnuson, Pasco, WA (US)

(73) Assignee: Battelle Memorial Institute, Richland, WA (US)

( * ) Notice: Subject to any disclaimer, the term of this patent is extended or adjusted under 35 U.S.C. 154(b) by 136 days.

(21) Appl. No.: 12/257,261

(22) Filed: Oct. 23, 2008

(65) Prior Publication Data

US 2009/0068723 A1    Mar. 12, 2009

Related U.S. Application Data

(62) Division of application No. 10/920,625, filed on Aug. 17, 2004, now Pat. No. 7,449,569.

(51) Int. Cl.
*C07H 21/04* (2006.01)
*C12N 15/63* (2006.01)

(52) U.S. Cl.
USPC ...................................... 536/24.1; 435/320.1

(58) Field of Classification Search
CPC .. C07H 21/04; C12N 15/63; C12Q 2525/143; C12Q 1/68
USPC ...................................... 435/320.1; 536/24.1
See application file for complete search history.

(56) References Cited

U.S. PATENT DOCUMENTS 7,439,067 B2   10/2008   Lasure et al.

FOREIGN PATENT DOCUMENTS

| WO | WO 03/100003 | 12/2003 |
| WO | PCT/US2005/028651 | 4/2007 |
| WO | PCT/US2005/028651 | 7/2007 |

OTHER PUBLICATIONS

Roberts et al. Expression of the *Escherichia coli* beta-glucuronidase gene in industrial and phytopathogenic filamentous fungi. Curr. Genet. 15:177-180, 1989.
Ebert et al., Proceedings of the National Academy of Sciences USA, 1987, 5745-5749, vol. 87.
Dai et al., "Identification of genes associated with morphology in *Aspergillus niger* . . . ," Applied Environmental Microbiology, 2004, 2474-2485, vol. 70.
Bennett and Lasure, eds., "More Gene Manipulations in Fungi," 1991, 441-458, Academic Press Inc, San Diego, USA.
Jefferson et al., European Molecular Biology Organization Journal, 1987, 3901-3907, vol. 6.

*Primary Examiner* — Michele K Joike
(74) *Attorney, Agent, or Firm* — Wells St. John P.S.

(57) ABSTRACT

The present invention encompasses isolated gene regulatory elements and gene transcription terminators that are differentially expressed in a native fungus exhibiting a first morphology relative to the native fungus exhibiting a second morphology. The invention also encompasses a method of utilizing a fungus for protein or chemical production. A transformed fungus is produced by transforming a fungus with a recombinant polynucleotide molecule. The recombinant polynucleotide molecule contains an isolated polynucleotide sequence linked operably to another molecule comprising a coding region of a gene of interest. The gene regulatory element and gene transcription terminator may temporally and spatially regulate expression of particular genes for optimum production of compounds of interest in a transgenic fungus.

19 Claims, 16 Drawing Sheets

FIG.1A

```
  1 ATCCACAGCAGATGGATCATAAGCAGTCAGACTGCAGGTCAGGTATCGGA          50
  1                                                              0

51 GTCCGAGACATTCGAACTAGTCTCCGACGCCACTGGAAAAATTCCTGCAC         100
  1                                                              0

101 TCGCCCACACGTGGTAAGCGATACGACTACATATTGTGTGGACAGAGGAA         150
  1                                                              0

151 TGTGGCCTCGAGCAGAGAAAGCTTGCCAACATGAAGATCACTGGCAGGCG         200
  1                                                              0

201 TGCTCATGAAAGCCATTCCGTGGGTTTTGTTTGGATAACCCGCAAGGTAC         250
  1                                                              0

251 ATACTCCGGGAGTGCTTGTCTCTTCAAGGTTCGCAGTATGACGGATCATC         300
  1                                                              0

301 TCCCTTGGTACGAAGGAAGGCATGTTATCAGTTATCGTGCCTTGTTAGTG         350
  1                                                              0

351 GCATTGGCAGTCGGAACGAGGGTCCACTAACCCAGTCAGGAACGAGGAAT         400
  1                                                              0

401 GAGCGACAGGAACCAGAGAATCTTCACCCAACATAGCGATGGATGATCTC         450
  1                                                              0

451 ATCGAGGACGTTGATCACCTCTCTCGCGGGGACTTTCAACGACGAACGGT         500
  1                                                              0

501 CAGTTTGCAGAATGAAACCCCCTTGACAATCTGTTGATCTGCGGCCAGTG         550
                                        ||||.||||||.|
  1                                     ctgcagccagcg           12

551 GGAAGAAA----GGAGGGAGTACGTGG---------------GTAGTAAC         581
    |||.||||    |||||||.|||||||               ||||||||
 13 ggaggaaaaaagggagggactacgtgggtagtagtagtagtagtagtaac         62

582 ATGACTTGTGTGTTTCTTGGTGTCTCTCCGTAGCAATTTAGGCGACCATC         631
    .||||        ||.||.||||.||||||||||||||||||||||.|||
 63 ctgac--------tttttgtgtttctccgtagcaatttaggcgactatc         104

632 CGATTACACGGGGGTGGAGACACCGGACAGGTTCCTTGGTGCCTTT----         677
    ||||||||||||||||.|||||||||||||||||||||||||||||
105 cgattacacgggggtggggacaccggacaggttccttggtgccttttgga         154
```

FIG. 1B

```
678  -------GGAGGACACGAGATGCGTTTAGTGCCTCTGGTCCCAATATTCG  720
            .||||||||||||||..||..||||||||||||||||||||||||
155  ctttaggagaggacacgagatggattgggtgcctctggtcccaatattcg  204

721  GAAGGTGGTAATTAAACTCTGTGCCTGGCCACTTCGGTGATTTAACGCTT  770
     ||| |||||||||||||||||||||||.||||||||||| |||||||||
205  gaa-gtggtaattaaactctgtgcctgtccacttcggtga-ttaacgctt  252

771  CGGCCTCGTGGCGTGTCTATGTCTCATTTGTGTCAAACCAGGACGCACCG  820
     |||||||||||||||||||||||||||||.||.||||||||..||||
253  cggcctcgtggcgtgtctatgtctcatttgtgccagaccaggactgaccg  302

821  GAAGCAGCTGGCAAGGCTCCGGAAGGCGAAGCCAATCAAGCACCACTCGA  870
     ||||.|||||||||||||||||||||||||||||||||||||||||..|
303  gaagaagctggcaaggctccggaaggcgaagccaatcaagcaccactta  352

871  TGAGGGGCACTGATCCATCCATTGTAAATTTTACATGAGGGTAATTTCCC  920
     |||||||||||||||||||||||.|||||.||||||||||||||||||
353  tgaggggcactgatccatccatcgtaaaatttacatgagggtaatttccc  402

921  AGGTAATTTGCCCTGC-GGCTATGTCATTGAGAATGGAAAAGTCTCCGGA  969
     |||||||||||||||| |||||||||||||||||||||||||||||||
403  aggtaatttgccctgcgggctatgtcattgagaatggaaaagtctccgga  452

970  TAATATTTGCCAAAAATGTGAGATGTGTGTGCGTG------------TG  1006
     ||.|||||||.|||||||||||||||||.|.|.|              ..
453  tattatttgccagaaatgtgagatgtgtgagagggaaaaaaaaaaaaaa  502

1007 TGAAAACGCTCGAGCTTCTGGAAGTGAAACAAAAGCTGAAAGGA--AAGG  1054
     ..||||||||||||||||||||||||||||.|||||| |||||.|||| ||||
503  aaaaaacgctcgagcttctggaagtgaaac-aaagctggaaggaggaagg  551

1055 AGGTG---GTGATGGCGA-TAATGGTGGTGGTGGTGGTGGTGTTTGTTTG  1100
     ||..|   |.|..|.||| .||.||.||| ...||.|||||||||||
552  agagggacgagcagacgaggaaaggaggt--aaatgatggtgtttgtttg  599
```

FIG.1C

```
1101 TTTGTTTGCGCGCGAATCCCTTGCGGGCCAAGTTCCACCAAC-GACTTCT 1149
     |||    ·||||||||||||||||||||||||||||||||||| ·||||||
 600 ttt-----tgcgcgaatcccttgcgggccaagttccaccaacaaacttct  644

1150 CTTTCTACTGTGTCTCTTCGTACTCCGTCCAGCTGCTGCTAGCCATCAAC 1199
     |||||||       ·|||||· |·| ||·||||·|          ·||||
 645 ctttcta-----actctttt-ttc-ccttccatc-----------acaac  675

1200 AACATCCTTCCTTCTCCGTTCTCGGGGTTCCTCCGTTGTTCCTGGCCTGG 1249
     ||||||||·|||||||||||||||||||||||||||||||||||·|·|||
 676 aacatcctcccttctccgttctcggggttcctccgttgttcctgacttgg  725

1250 TCTGACATAAGGTTATGATTGTTTCACATGTCCCACGGCTTCGCCGGCTT 1299
     |||||||||||||||||||||||||·|||||||||!|||||||||||||||
 726 tctgacataaggttatgattgtttcacttgtcccacggcttcgccggctt  775

1300 GGAGCTGAGACCCTCTTCTGAGTC-AATGGTACCATTTTGCCGAATTCGT 1348
     ·|||||||||||||||||||||||| ||||||||||||||||||··||||
 776 agagctgagaccctcttctgagtcaaatggtaccattttgccgatatcgt  825

1349 GGCTAGTTCTC-TATTTCTATGCTCTTGACTTTGGTACCGTTGGCATTAG 1397
     ||||||||||| ||·||·||·|||||·||·|·||||||||||||||||||
 826 ggctagttctcttacttttacgctctggattatggtaccgttggcattag  875

1398 TTTGATC-------TACTAATAAAGAGCCTAGTTTTAGGCGAATATACAC 1440
     |||||||       ||||||||··|||||||||||||·||||||||
 876 tttgatctattccgtactaataacaagcctagttttaggcggatatacac  925

1441 TGTTACCCACCGGGTAGTATTCAGTAGCTAC--CCTCCCACTCCCC--AG 1486
     |||||||| |·|||||·||||||||··|||   ||||||||·|·|  ||
 926 tgttaccca-caggtagcattcagtaaatacctcctcccactactcttag  974

1487 GCTCCCACGCTGAGAGCCTTGATTCGATGTCTCTCCTAAAATTGCTAGGC 1536
     ||||||||||||·||||||||||||||||||||||||||||||||·||||
 975 gctcccacgctcagagccttgattcgatgtctctcctaaaattgccaggc 1024
```

FIG.1D

```
1537 TGTTAGCGCCCTGGCAGATGAACCCCCGCTCATCCCTCGTATATGCGG--    1584
     ||||||||||||||||||||||||||||||||||||||||||||·|||||
1025 tgttagcgccctggcagatgaaccccgctcatccctcgtatctgcggtc    1074

1585 --------TCTCAATTTCTGAGTGGCCCACGCCT-CCGAGTATCTTTGAG    1625
             |||||||||||||||||||||||||| |||||||||||||||
1075 tcaatttatctcaatttctgagtggcccacgcctcccgagtatctttgag    1124

1626 CACATCCACGATGGAGGGAGGCGATCCAAGCGGTCTAACAGCGGACTAAA    1675
     ||·|||||||||||||··|||||||||||||·||||||||||||||||||
1125 catatccacgatggaggggagcgatccaagcggactaacagcggactaaa    1174

1676 CCGCTCTGTGTAAGCCAGTCAGAGAGTCATACTGGCTTGAGGTGACATCG    1725
     |||| | |||||||||||||||||||||||||||||||||||||||||||
1175 ccgc-c-gtgtaagccagtcagagagtcatactggcttgaggtgacatcg    1222

1726 CCAATTCATTTCACAAGGTTTAGTCGGGGGAGGGTAGGCCCCATACATTC    1775
     ||·|||||||||·|||||||||||||||·|||||||||||||||||||||
1223 cctattcatttcgcaaggtttagtcggggaagggtaggccccatacattc    1272

1776 CACCGTTCTCAAAGTTTACCAGGCATTTCTCACACTAACCATGCAATAGT    1825
     ||||||||||||||||||||||·|||·|||·|·|||||||||||||||||
1273 caccgttctcaaagtttaccagacatctcttagactaaccatgcaatagt    1322

1826 AGGTAACTAGCAGTAGTCTTGAACGCTGTTCCTGAGCAAGTTCCCAATCA    1875
     ||||||||||||||||||||||||||||||||||||||||||||||||||
1323 aggtaactagcagtagtcttgaacgctgttcctgagcaagttcccaatca    1372

1876 GCAATT----TGAAAGAATAATTTCCTTTGACCCACCGGGTAAATGAGCC    1921
     ||||||    |||||||||||||||·|||||||||||||| |||||||||
1373 gcaatttgaatgaaagaataatttcccttgacccaccggg-aaatgagcc    1421
```

FIG. 1E

```
1922 GCAGATTTGGCGATGTTGGGCTCGGAGCCTGGTAGGTAGTAGTGAATGTC 1971
     ||||||||||||||||||||||||·|||||||||||||·|||||||||||
1422 gcagatttggcgatgttgggcttggagcctggtaggttgtagtgaatgtc 1471

1972 ATCCCCTCCATAGGGGGGAATT--GGGAGGGGGGCTGTGAATGGACTTGT 2019
     ||||||||||||||||||||||  |·|||||||||||||·|||||||||
1472 atccctccatagggggggaattgagagaggggggctgtgaagggacttgt 1521

2020 CCTACGCCTGTCGCATCCCCATCATTCATATACTTGAATG-TCTCTTCTC 2068
     ||||||||||·|||||||||||||||||||||||||||| ||··|||·|
1522 cctacgcctgtcacatccccatcattcatatacttgaatgttcctttccc 1571

2069 CCCCCTCCTCCTTCTCTTTCTCTCCTTCCCTTCTCACGATTTGACGTCCC 2118
     ||||||||||||||||||||||||·|||||||||||||||||||||||||
1572 cccctcctccttctctttctctcgttcccttctcacgatttgacgtccc 1621

2119 TCGCGTTTTCGCCCTCTCCCACGGTAGTCACTCCTTTGCACTACATACAC 2168
     ||||·|||||||||||||||||||||||||||||||||||||||||||||
1622 tcgcattttcgccctctcccacggtagtcactcctttgcactacatacac 1671

2169 GAAGTCTTACTTCCAGTCACTCTTTGAA-ACCACTTCTCAATATCCCTAC 2217
     |||||·|||||||||||||||||||||| ··|||···|||||||||||
1672 gaagttttacttccagtcactctttgaattacactctccaatatccctac 1721

2218 CTCTTATCATTCTTTACTTCACGCACAAGACACGAAAGTgaacctgtaaa 2267
     ||··||||||||||||·||||·|||||||||||||||||···|·|||
1722 ctactatcattctttacatcacacacaagacacgaaagtgaaatcgaaaa 1771

2268 aatg                                               2271
     ||||
1772 aatg                                               1775
```

US 8,735,562 B2

ISOLATED FUNGAL PROMOTERS AND GENE TRANSCRIPTION TERMINATORS AND METHODS OF PROTEIN AND CHEMICAL PRODUCTION IN A FUNGUS

STATEMENT REGARDING FEDERALLY SPONSORED RESEARCH OR DEVELOPMENT

This invention was made with Government support under contract DE-AC0676RLO-1830, awarded by the U.S. Department of Energy. The Government has certain rights in this invention.

RELATED PATENT DATA

This application includes a sequence listing provided on compact disc file 14289-E.prj, file size 39.2 KB, hereby incorporated by reference.

TECHNICAL FIELD

The invention pertains to isolated polynucleotide molecules of gene regulatory elements in filamentous fungi. More specifically, the present invention relates to isolation of filamentous fungal promoters and gene transcription terminators, construction of recombinant polynucleotide constructs, and methods for protein and chemical production in a fungus.

BACKGROUND

Fungi are increasingly important in the production of many commercially-useful products. For example, filamentous fungi currently produce a number of metabolites on the industrial scale including antibiotics such as penicillins and cephalosporins, and organic acids such as citric and fumaric acids. Filamentous fungi are also used for the industrial production of enzymes such as proteases and lipases.

Utilization of a filamentous fungus species for production of a desired compound often involves growing submerged cultures of the fungus. Filamentous fungi can exhibit numerous morphologies in submerged cultures, including pelleted and "filamented" morphologies. When fungi in culture exhibit a filamented morphology, the presence of the filaments can increase the viscosity of the culture medium. The increased viscosity can affect the mass transfer and aeration properties of the culture, cause mixing problems in a bioreactor, and result in decreased productivity.

Alternatively, filamentous fungi can exhibit a pelleted morphology. In contrast to cultures of fungi exhibiting a filamented morphology, fungi cultures exhibiting a pelleted morphology can have relatively low viscosities and require substantially less power for mixing and aeration of the culture. Productivity for many compounds, for example citric acid, itaconic acid, statins, penicillins, and various enzymes, can be enhanced by utilizing fungus exhibiting a pelleted morphology. However, in certain fungal species, production of chemicals, for example peptic enzymes or fumaric acid, can be enhanced by utilizing a fungus exhibiting a filamented morphology. Typical practices in fungus-assisted chemical/protein production do not deliberately control the morphology of the fungus.

During fungal-morphology formation, a series of genes are up regulated or down regulated. To achieve optimal production of chemicals and/or proteins of interest, one can utilize the promoters and transcription terminators that exhibit strong constitutive expression of those genes. Concurrently, one can utilize induced gene expression at specific culture conditions and key stages in the cell's development to maximize gene expression and minimize adverse effects on fungal growth that may be associated with the enhanced production of certain chemicals and/or proteins. Thus a need exists for isolated fungal promoters and transcription terminators for regulation of gene expression in a fungus as well as methods for promoting enhanced production of desired chemicals and proteins.

SUMMARY

In view of the foregoing and other problems, disadvantages, and drawbacks of traditional chemical and protein production in a fungus, the present invention has been devised. The invention encompasses isolated polynucleotide molecules comprising polynucleotide sequences that regulate the expression of genes that are differentially expressed in a native fungus exhibiting a pelleted morphology relative to a filamented morphology. In one aspect, the invention encompasses promoters that possess strong, constitutive activity in genes that are differentially expressed in native fungi exhibiting a pelleted morphology relative to a filamented morphology. The invention also encompasses inducible gene promoters that, for example, initiate expression at certain developmental stages in the native fungus. In another aspect, the invention encompasses transcription terminators from genes that are differentially expressed in native fungi exhibiting the pelleted morphology relative to native fungi exhibiting the filamented morphology.

One object of the present invention is to introduce new genetic material into eukaryotic organisms such as filamentous fungi to establish new strains for use in production of chemicals and/or proteins.

Another object of the present invention is to regulate the morphology formation in filamentous fungi.

A further object of the present invention encompasses a method for constitutive production of a compound, such as in chemical and protein production utilizing a transformed host cell.

A still further object of the present invention encompasses a method of induced production of a compound from a transformed host cell.

Another object of the present invention is to use the isolated *Aspergillus niger* (*A. niger*) promoters to regulate expression of foreign genes as well as reintroduced native genes for chemical or protein production.

DESCRIPTION OF DRAWINGS

Preferred embodiments of the invention are described below with reference to the following accompanying drawings.

DETAILED DESCRIPTION

Figure 1:
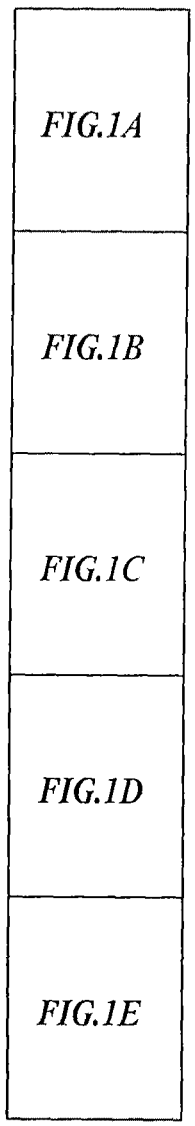
FIGS. 1A-1E compare the isolated nucleotide sequences for the promoter region of the *A. niger* Balu-42 gene, SEQ ID NO: 50 (top sequence), and for the promoter region of the *Aspergillus kawachii cwpB* gene SEQ ID NO: 62 (bottom sequence) for a hypothetical protein.

For a clear and concise understanding of the specification and claims, including the scope given to such terms, the following definitions are provided:

The filamentous fungi of the present invention are eukaryotic microorganisms and include all filamentous forms of the subdivision Eumycotina. A vegetative mycelium composed of chitin, cellulose, and other complex polysaccharides characterizes these fungi. The filamentous fungi of the present invention are morphologically, physiologically, and genetically distinct from yeasts. Vegetative growth by filamentous fungi is by hyphal elongation while carbon catabolism is obligately aerobic. Various species of filamentous fungi from the three major fungal groups may be used as expression hosts including Basidiomycetes, Ascomycetes, and Zygomycetes. An exemplary member of the Basidiomycetes group is *Phanerochaete chrysosporium*. Exemplary members of the group of Ascomycetes and Imperfect Fungus include *Aspergillus niger, Aspergillus oryzae, Aspergillus terreus, Emericella nidulans, Neurospora crassa, Fusarium oxysporum, Penicillium chrysogenum*, and *Trichoderma reesei*. Exemplary members of the Zygomycetes group include but are not limited to *Rhizomucor miehei* and *Rhizopus oryzae*.

As used herein, the terms filamented and pelleted can refer to the morphology of filamentous fungi. Thus, filamentous fungi can be characterized by having a filamented morphology or a pelleted morphology.

As used herein, a morphology-enhanced promoter can refer to a DNA sequence that, when operably linked to a gene, can exhibit enhanced promoter activity and increased transcription of that gene in a specific morphology compared to some or all other morphologies in an organism. For example, a pelleted-enhanced promoter is a DNA sequence that directs a relatively higher level of transcription for genes associated with a pelleted morphology. An analogous term can be applied to transcription terminators.

A cloning vector is a DNA molecule, such as a plasmid, cosmid, or bacteriophage, which has the capability of replicating autonomously in a host cell. Cloning vectors typically contain one or a small number of restriction endonuclease recognition sites at which foreign DNA sequences and marker genes can be inserted in a determinable fashion without loss of an essential biological function of the vector. The marker gene aids in the identification and selection of cells transformed with the cloning vector. Marker genes can typically include genes that provide tetracycline, kanamycin, or ampicillin resistance.

A transgene expression vector can mean a DNA molecule comprising a foreign gene that the host cell expresses. Typically, certain regulatory elements, which include constitutive or inducible promoters, morphology-specific regulatory elements and enhancers, and transcription terminators control expression of the gene. Such a gene is said to be "operably linked to" the regulatory elements.

A recombinant host can be any prokaryotic or eukaryotic cell that contains one or more recombinant DNA molecules, whether or not the DNA is genomically integrated. This term also includes those prokaryotic or eukaryotic cells that have been genetically engineered to contain the cloned gene(s) in the chromosome or genome of the host cell.

A transgenic fungal strain is a fungal strain having one or more fungal cells that contain a foreign gene. In eukaryotes, RNA polymerase II catalyzes the transcription of a structural gene to produce mRNA. A DNA molecule can be designed to contain an RNA polymerase II template in which the RNA transcript has a sequence that is complementary to that of a specific mRNA.

Constitutive can refer to continuous expression of a gene without any regulation. When used in conjunction with a particular morphology, it can also refer to expression of a gene under all conditions for that morphology.

Homology can refer to the degree of similarity between sequences of nucleic acids or amino acids with regard to positional identity. It can also refer to the concept of similar functional properties among different nucleotide or amino acid sequences.

Foreign gene as used herein can refer to genes from other organisms as well as native genes that are re-introduced to the organism.

Heterologous can refer to aspects, for example, gene expression or proteins, that derive from or relate to different organisms.

The present invention encompasses nine promoters and seven transcription terminators discovered in a fungal strain, *Aspergillus niger* (*A. niger*), which is a citric-acid-producing organism. The nucleotide sequences for the pelleted-enhanced promoters for the Arsa-7, A-37, Arsa-43, and A-90 genes as well as the filamented-enhanced promoters for the Brsa-25, Brsa-47, Brsa-109, and Brsa-118 genes are set forth in SEQ ID NOs. 46-49 and 51-54, respectively. The nucleotide sequence for the promoter for the Balu-42 gene is set forth in SEQ ID NO: 50 and has a 66.9% identity to the promoter region of *Aspergillus kawachii* cwpB gene for a hypothetical protein, as shown in FIGS. 1A-1E. The length of filamented-enhanced gene promoter Balu-42 is 2271 base pairs. Based on a Basic Local Alignment Search Tool (BLAST) search, the remaining promoters show no homology to any known promoters in the GeneBank database, the European Molecular Biology Laboratory-European Bioinformatics Institute (EMBL-EBI) fungi nucleotide database, or the genome database of *A. nidulans, N. crassa*, and *M. grisea*.

The nucleotide sequences for the three filamented-enhanced transcription terminators for the Brsa-25, Brsa-47, and Brsa-118 genes, as well as the four pelleted-enhanced transcription terminators for the Arsa-7, A-37, Arsa-43, and A-90 genes are set forth in SEQ ID NOs. 59-61 and 55-58, respectively. These transcription terminators do not show any significant similarity to known sequences in the GeneBank database, the EMBL-EBI fungi nucleotide database, or the genome database of *A. nidulans, N. crassa*, and *M. grisea*. The genes associated with the 16 regulatory elements encompassed by the present invention are described in published U.S. patent application Ser. No. 10/442,017, titled "Isolated Polynucleotides and Methods of Promoting a Morphology in a Fungus" by Lasure et al., the contents of which are herein incorporated by reference.

The actual promoter fragments and transcription terminators comprising the polynucleotide sequences set forth in SEQ ID NOs. 46-61 were obtained from *A. niger* strain number 11414 at the American Type Culture Collection (ATCC11414). Culture samples of *A. niger* (filamented morphology) were harvested two days after inducement. The samples were centrifuged to form culture pellets, which were frozen with liquid nitrogen and stored at −80° C. for total genome DNA extraction. Total genomic DNA of *A. niger* was extracted by the cetyltrimethylammonium bromide (CTAB) method.

Genome walking served as an effective means for isolating the desired nucleotide sequences. Briefly, the technique consists of digesting genomic DNA with restriction endonuclease Dra I, EcoR V, Puv II, or Stu I and linking the respective fragments with an adaptor oligonucleotide to form four genome walking libraries named DraI, EcoRV, PvuII, or StuI library, respectively. A gene-specific primer (GSP) and an adaptor primer provided by the manufacturer of the GENOMEWALKER™ kits (Clontech Laboratories, Inc., Palo Alto, Calif.) were used to isolate the gene-specific promoter or transcription terminator fragments. The genomic DNA sequence was determined by sequencing the DNA polymerase chain reaction (PCR) products. One GSP was designed for promoter isolation and another one for gene transcription terminator isolation.

Once identified, each of the promoters and transcription terminators described above can be operably linked to additional DNA segments to form DNA constructs. A first DNA segment comprising at least a portion of a functional promoter sequence encompassed by the present invention (SEQ ID NO: 46-54) can be operably linked to a second DNA segment comprising a DNA sequence coding a protein of interest. For example, the second DNA segment may comprise a GUS reporter gene or it may comprise a coding sequence that is differentially expressed in a native fungus exhibiting a pelleted morphology relative to the native fungus exhibiting a filamented morphology. Alternatively, the second DNA segment can comprise a sequence encoding a protein of interest which is not natively expressed in fungus, or which does not exhibit morphology-based differential expression in native fungus. Specific examples of proteins of interest include, but are not limited to cellulases, amyglucosidases, amylases, lipases, microbial rennets, xylanases, galactosidases, mannanases, glucanases, phytases, monoclonal antibodies, bovin serium albumin and human blood coagulation-associated proteins. Furthermore, the 3'-end of the second DNA segment in the construct can be operably linked to a third DNA segment comprising a transcription terminator. In a preferred embodiment, the third DNA segment comprises at least a portion of a transcription terminator encompassed by the present invention (SEQ ID NO: 55-61).

The present invention can also encompass a vector. A non-limiting example of such a vector can be one that will produce a fungus carrying the DNA sequence of interest, and can comprise, though at low efficiency, a naked piece of DNA capable of conferring the properties of this invention. Another example of a vector includes a transgene expression vector for the fungal strain, *Aspergillus niger*, which utilizes one of the native promoters to regulate the expression of a β-glucoronidase (GUS) reporter gene in *A. niger*. Further, this vector can be used as a chromosomal integration vector for other foreign gene expression in *A. niger*.

Additional examples of vectors can comprise the DNA construct as described above as well as lactate dehydrogenase cDNA from *Rhizopus oryzae* for lactic acid production in *Aspergillus niger*, genes of cellulases from *Trichoderma reesei*, cDNA of hen egg-white lysozyme (HEWL), and cDNA of single chain Fv (scFv) antibody fragments. The DNA fragments, which comprise the coding sequences of any of genes of interest, can be inserted between the 5'-end and the 3'-end of a promoter and a transcription terminator, respectively, of the present invention.

The constructs and vectors as described above can utilize promoter sequences of the present invention having strong, constitutive activity or inducible gene promoters that, for example, initiate expression at certain developmental stages in the native fungus. Examples of developmental stages can include, but are not limited to vegetative, sexual, pelleted morphology formation, and filamentous morphology formation. The early pelleted morphology formation stage can occur approximately 6 to 12 hrs after inoculation of spores into culture medium. Late pelleted morphology formation stage can occur, for example, 3 days after inoculation of spores into the culture medium The particular method of transformation typically guides selection of an appropriate vector, or whether to even use a vector. For example, a heterologous nucleic acid sequence can be introduced into a fungal cell utilizing *Agrobacterium tumefaciens* containing a Ti plasmid. When using an *A. tumefaciens* culture as a transformation vehicle, it can be most advantageous to use a non-oncogenic strain of the *Agrobacterium* as the vector carrier so that normal non-oncogenic differentiation of the transformed cells is possible. It can also be preferable to have the *Agrobacterium* harbor a binary Ti plasmid system. The binary system comprises 1) a first Ti plasmid having a virulence region that is essential for the introduction of transfer-DNA (T-DNA) into fungi, and 2) a chimeric plasmid. The chimeric plasmid contains at least one border region of the T-DNA region of a wild-type Ti plasmid flanking the nucleic acid to be transferred. Binary Ti plasmid systems have proven to be effective in transforming fungal cells. Such a binary system can be preferred because it typically does not require integration into the Ti plasmid in *Agrobacterium*.

Methods involving the use of *Agrobacterium* include, but are not limited to: 1) co-cultivation of *Agrobacterium* with fungal spores; 2) transformation of fungal cells or tissues with *Agrobacterium*; and 3) transformation of fungal protoplasts with *Agrobacterium*.

The construct described herein can also be introduced into a fungal cell chemically through contact between the cell and the construct. For example, nucleic acid may be transferred into fungal cells using polyethylene glycol/$CaCl_2$-mediated genetic material uptake by the fungal cell. Alternatively, the nucleic acid can be introduced into fungal cells by electroporation. In this technique, fungal protoplasts are electroporated in the presence of vectors or nucleic acids containing the relevant nucleic acid sequences. Electroporated fungal protoplasts can reform the cell wall, divide and form fungal tissues. Selection of the transformed fungal cells with the transformed gene can then be accomplished using phenotypic markers. The nucleic acid can also be introduced into fungal cells by microprojectile particle bombardment (biolistic) transformation. The nucleic acid can be coated on particles for nucleic acid delivery by rupture discs. The particles can comprise tungsten (M5) while the rupture discs can be, for example, 1100-psi rupture discs. The optimal distance between the rupture disc and the tungsten particle carrier and between the launch assembly and target cells can be adjusted to suit different fungal cells.

The vectors described above can be used to facilitate the expression and/or secretion of heterologous proteins in fungal fermentation culture. Fungal cells comprising a transgene expression vector that allows high-level expression of a protein product of interest can be placed and maintained into fungal fermentation cultures and induced using appropriate agents. The protein of interest can be mammalian proteins, plant proteins, fungal proteins, or bacterial proteins, including, but not limited to, human blood factor proteins, plant proteases, fungal cellulases and hemicellulases, and thermally-stable DNA polymerases of bacteria, respectively. The result can be high-level production of the desired heterologous protein. Techniques for isolating the heterologous proteins can include, but are not limited to fractional precipitation, various chromatographies, and ultracentrifugation. In some cases, the proteins produced by the transgenic fungal cells are not the desired product, but are used rather to enhance production of another chemical. In such instances, the transgenic fungal cells of the present invention can be allowed to produce proteins, for example, enzymes, that enhance production of the desired chemical. Chemicals of interest can include, but are not limited to acids and statins. Examples of acids can include aconitic acid, citric acid, fumaric acid, itaconic acid, malic acid, succinic acid, oxalic acid, gluconic acid, and lactic acid. Examples of statins can include lovastatin and compactin By combining the technology of the present invention with production methods described herein as well as those that are well-established (e.g., fungal fermentation and product recovery), chemical compounds and recombinant proteins can be efficiently and economically produced for the biopharmaceutical, industrial processing, animal health, and bioremediation industries. The following examples are given to illustrate the present invention. It should be understood that the invention is not to be limited to the specific conditions or details described in these examples.

EXAMPLE 1

Isolation of Fungal Promoters and Transcription Terminators

Figure 2:
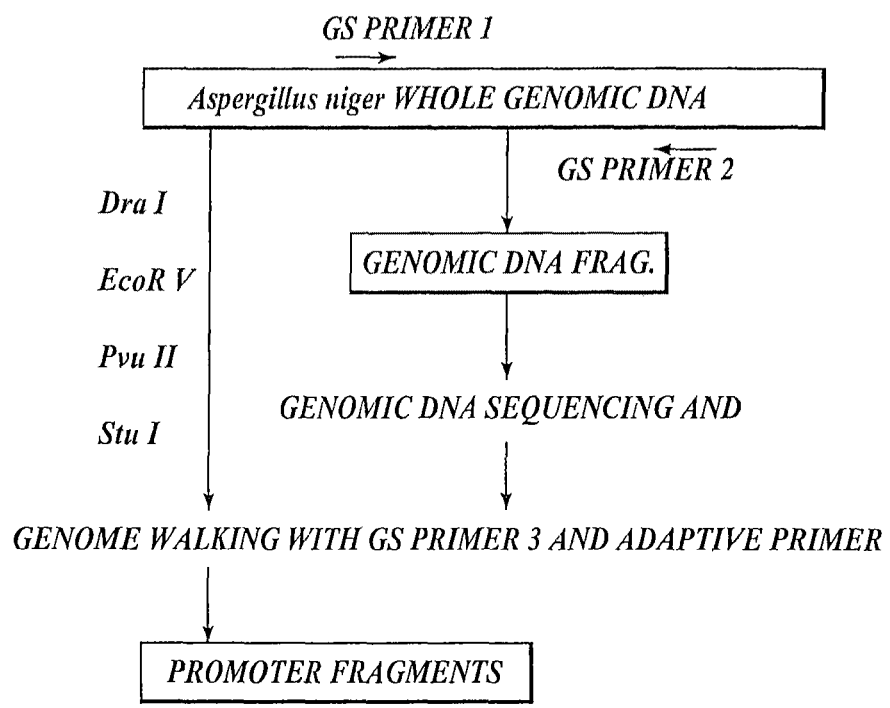
FIG. 2 is an illustration of the procedure for promoter and transcription terminator sequence isolation by genome walking.

The *A. niger* (ATCC11414) cells were grown in a liquid flask culture with non-citric acid production media containing 1000 ppb $Mn^{2+}$, 140 g/l glucose, 3.1 g/l $NH_4NO_3$, 0.15 g/l $KH_2PO_4$, 0.15 g/l NaCl, 2.2 g/l $MgSO_4.7H_2O$, 6.6 mg/l $ZnSO_4.7H_2O$, and 0.1 mg/l $FeCl_3$ adjusted to pH 2.0 with 4 M $H_2SO_4$. The biomass was then harvested by centrifugation and the genomic DNA was isolated by the CTAB method. Based on cDNA sequences of *A. niger* genes identified in U.S. patent application Ser. No. 10/442,017, two sets of gene-specific primers, GSP-1 (SEQ. ID NO.: 1-9) and GSP-2 (SEQ. ID NO.: 10-18) at 5'-end and 3'-end, respectively, were designed, synthesized, and used to isolate genomic DNA fragments of a specific gene by genomic PCR. The DNA sequences of specific genome DNA fragments were determined by conventional DNA sequencing. As shown in FIG. 2, the genomic DNA sequence was used as a source DNA sequence to design additional primers (SEQ. ID NO.: 19-34), designated generally as gene specific primers-3 (GSP-3) for isolation of fungal promoters or transcription terminators via genomic PCR. Table 1 lists the sequences for each of the gene specific primers as well as the adaptor primers.

The genomic DNA was first digested separately with restriction endonucleases Dra I, EcoR V, Pvu II, or Stu I. This digestion generated a series of genomic DNA fragments with blunt ends. After generation of the blunt-end fragments, a GENOMEWALKER™ adaptor oligonucleotide of 48-base pairs was linked to the ends of genomic DNA fragments to generate four separate genome-walking libraries. The libraries were designated as Dra I, EcoR V, Pvu II, and Stu I, respectively. The genome-walking libraries were used as genomic DNA templates for genomic PCR with adaptor primer 1 (SEQ. ID NO. 35) or 2 (SEQ. ID NO.: 36) and the appropriate GSP-3 fragment (SEQ ID NO: 19-34). The PCR fragments were separated by low melting point agarose gel electrophoresis and isolated by gelase digestion and a micro-con centrifugal device. The PCR fragment was then inserted into the pGEM-Teasy vector for DNA replication and DNA sequencing. The PCR fragments were aligned with known genome DNA sequences using the BLAST 2 program to verify the identity of the newly isolated promoter or transcription terminator fragment.

TABLE 1

Oligonucleotides (GSP-1, GSP-2, GSP-3, and adaptor primers) used for promoter and transcription terminator isolation

| SEQ ID NO: | Gene | Oligonucleotide name | Oligonucleotide |
|---|---|---|---|
| | | Gene specific primer (GSP-1) used for genome DNA isolation | |
| 1 | Balu-42 | FP-35 (Balu42-5P) | 5'-CCA CGG TAG TCA CTC CTT TGC ACT A-3' |
| 2 | Brsa-25 | FP-37 (Brsa25-5P) | 5'-CCT CTA TTC TGT CTC CCT TCG GCG AT-3' |
| 3 | Brsa-47 | FP-51 (Brs47-P5) | 5'-GCA ATC GTC TTC CCG TCG TTC A-3' |
| 4 | Brsa-109 | FP-55 (Brs109-P5) | 5'-GTC TGT CGT GGT GTC GTA TCA AAT G-3' |
| 5 | Brsa-118 | FP-39 (Brsa118-5P) | 5'-CTC CTT CTT CCC CCC CAT ACA TCA-3' |
| 6 | Arsa-7 | FP-47 (Arsa-7-P5) | 5'-GCT GTG CTT CGT ACC TTC ATT TCG-3' |
| 7 | A-37 | FP-43 (A37-5P) | 5'-GCC ATC TAT CAA CAC GAG AGA AAA C-3' |
| 8 | Arsa-43 | FP-95 (Arsa43-5P) | 5'-TGC AGA TCT TCG TTA AGA CCC TCA C-3' |
| 9 | A-90 | FP-57 (A90-5P) | 5'-CTC TCC CAC CTC CCC AGC CTT TCC T-3' |
| | | Gene specific primer (GSP-2) used for genome DNA isolation | |
| 10 | Balu-42 | FP-36 (Balu42-3P) | 5'-GAG TCG ACG AAT CGA ATC GAA TCG-3' |
| 11 | Brsa-25 | FP-38 (Brsa25-3P) | 5'-GAC ACC ATC ACA GAC ATA TAC AGA GA-3' |
| 12 | Brsa-47 | FP-52 (Brs47-P3) | 5'-CAA AGA GTG GCT GTA GTT GGC T-3' |
| 13 | Brsa-109 | FP-56 (Brs109-P3) | 5'-GTG CCC ATC AGA AGT GAA CCA AGA-3' |
| 14 | Brsa-118 | FP-40 (Brsa118-3P) | 5'-GCA TTC CAG CTC CTG TCT GGA CAA-3' |
| 15 | Arsa-7 | FP-48 (Arsa-7-P3) | 5'-CAC AAG CGT CCA ATC CAT CAC A-3' |
| 16 | A-37 | FP-44 (A35-3P) | 5'-GAG AGG ATC GAC AAG GTA ACA TTC CAG AA-3' |
| 17 | Arsa-43 | FP-96 (Arsa43-3P) | 5'-GCG GAG GAC AAG ATG GAG AGT AGA C-3' |
| 18 | A-90 | FP-58 (A90-3P) | 5'-CCA AGG TAA AGC AGA TCT AAT GG-3' |
| | | Gene specific primer (GSP-3) used for promoter isolation | |
| 19 | Balu-42 | FP-79 (Balu-42R) | 5'-ACT TTC GTG TCT TGT GCG TGA AGT AA-3' |
| 20 | Brsa-25 | FP-81 (Brsa-25R) | 5'-GGT TTC TTT ATC CTG TCC GTA TGC TG-3' |
| 21 | Brsa-47 | FP-85 (Brsa-47R) | 5'-GAC GGT TTA TAT TCG ACC ACG CCT CA-3' |
| 22 | Brsa-109 | FP-87 (Brsa-109R) | 5'-GCT AGT GGC CTT CAT TGT TGT ATG AG-3' |
| 23 | Brsa-118 | FP-89 (Brsa-118R) | 5'-TGA ATG TGT AAA AGG AGG AGG GGT AA-3 |
| 24 | Arsa-7 | FP-91 (Arsa-7R) | 5'-AGT AAG GCG AAA TGA AGG TAC GAA GC-3' |
| 25 | A-37 | FP-93 (A-37R) | 5'-CAG CAG CAG ACA TTG TGA TGT GAT AG-2 |
| 26 | Arsa-43 | FP-99 (Arsa-43R) | 5'-GAT GCC CTC CTT ATC CTG GAT CTT G-3' |
| 27 | A-90 | FP-105 (A-90R) | 5'-GCG GTC AGA AGA GAC TTG AAG GAG AC-3' |
| | | Gene specific primer (GSP-3) used for transcriptional terminator isolation | |
| 28 | Brsa-25 | FP-82 (Brsa-25L) | 5'-CTG TGG AGT AGA TGG GCA CTC TTG AT-3' |
| 29 | Brsa-47 | FP-86 (Brsa-47L) | 5'-CAC CCA CCT AGT AAT GCT TAG CCA TC-3' |
| 30 | Brsa-118 | FP-90 (Brsa-118L) | 5'-TTT GTG GTT CGC CTT AAT AGA GCT TG-3' |
| 31 | Arsa-7 | FP-92 (Arsa-7L) | 5'-ATC ATC TGA CGC TGA TGC AAT AGT TC-3' |
| 32 | A-37 | FP-94 (A-37L) | 5'-GGA CAT GGA CAT GGA TAT GAG TTT GA-3' |
| 33 | Arsa-43 | FP-100 (Arsa-43L) | 5'-CTT TAG CAC GGC TCA TCT ACG GTT G-3' |
| 34 | A-90 | FP-104 (A-90L) | 5'-TTG AGC TCG AGT GGA AAG GTC TAC G-3' |
| 35 | | Adaptor primer-1 | 5'-GTA ATA CGA CTC ACT ATA GGG C-3' |
| 36 | | Adaptor primer-2 | 5'-ACT ATA GGG CAC GCG TGG T-3' |

TABLE 1-continued

Oligonucleotides (GSP-1, GSP-2, GSP-3, and adaptor primers) used for promoter and transcription terminator isolation

| SEQ ID NO: | Gene | Oligonucleotide name | Oligonucleotide |
|---|---|---|---|
| | | Gene specific primer used for deletion of ATG-transcription start site at the promoter fragment's 3'-end | |
| 37 | Arsa-7 | FP-135 (pArsa-7-412H5) | 5'-TCA AGC TTC TGC TCC AAC GCG CTA TCA AAT CGA A-3'C-3' |
| 38 | Arsa-7 | FP-136 (pArsa-7-2040P3) | 5'-CAC AGC TGA TTG AAA GAA TAG AGA GTG ATG GAG TTG-3' |
| 39 | A-37 | FP-125 (A-37-P-XbaRI) | 5'-CGG AAT TCT CTA GAG TGA TGT GGA TAG GGA TGG GAA TAA G-3' |
| 40 | Arsa-43 | FP124 (Arsa-43-P-Cla-H3) | 5'-CCA AGC TTA TCG ATG TTG TAG AAG CGC AGT TAA TGG TGT ATG-3' |
| 41 | Brsa-25 | FP-152 (Brsa25-1677Sma) | 5'-ATC CCG GGT AAA GCA AGG CGA ATG ACG AAG ACA-3' |
| 42 | Brsa-109 | FP-137 (PBrsa-109-23S5) | 5'-CAG AGC TCC TCC TGT CTG AGT GTT GTC TCA-3' |
| 43 | Brsa-109 | FP-138 (pBrsa-109-1835P3) | 5'-CTC AGC TGT TGT ATG AGA GGT GTA TAT GTA TGT-3' |
| 44 | Brsa-118 | FP-155 (Brsa118-1502pml) | 5'-GCA CGT GAA TGT GTA AAA GGA GGA GGG GTA-3' |
| 45 | | T-7 primer | 5'-TAA TAC GAC TCA CTA TAG GG-3' |

EXAMPLE 2

This example describes the steps taken to prepare different fungal promoters fused in front of a GUS reporter gene with the 3'-TtripC transcription terminator. Use of the constructs produced according to this example demonstrates the function of different promoters and their potential use in the production of different proteins and chemicals via various fungi.

Figure 3:
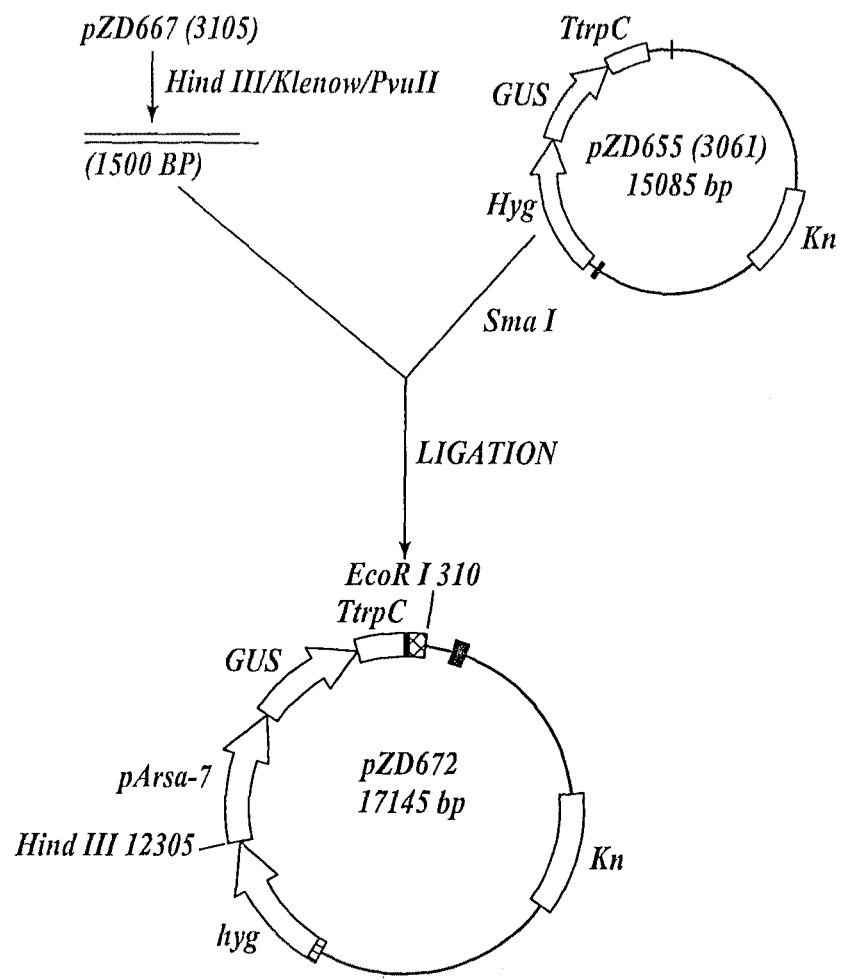
FIG. 3 is a schematic illustrating a plasmid vector pZD672, which contains the promoter region of the pelleted-associated Arsa-7 gene (SEQ ID NO: 46) and the β-glucoronidase (GUS) reporter gene, for *Agrobacterium*-mediated transformation in *A. niger*.

Since the GUS reporter gene contains its own ATG-translation start site, in the transgene expression vector, introduction of a proper restriction endonuclease site at the 3'-end of the promoter was preceded by removal of the ATG-translation start site from all the promoter fragments being prepared for function analysis. PCR fragments were cloned into the pGEM-Teasy vector and the presence of the promoter fragment was confirmed by restriction endonuclease digestion. The promoter fragment released by restriction endonucleases was inserted into binary vectors pZD640 or pZD655 for *Agrobacterium*-mediated transformation. The method of construction for specific vectors for *Agrobacterium*-mediated transformation is described as follows:

The PCR fragment containing the promoter for the pelleted-associated Arsa-7 gene (SEQ ID NO: 46) was first isolated via genome walking with gene specific primer FP-91 (SEQ ID NO: 24) and subsequently cloned into pGEM-Teasy vector to form pZD611. The plasmid DNA was then sequenced to confirm the newly isolated fragments. In order to remove the ATG-transcription start site at the promoter fragment's 3'-end, pZD611 was used for a template for PCR with primer FP-135 (SEQ ID NO 37) and FP-136 (SEQ ID NO: 38). Referring to FIG. 3, the PCR product was inserted into pGEM-Teasy to form pZD667. Then the Arsa-7 promoter fragment (SEQ ID NO: 46) was excised by Hind III and Pvu II and treated with DNA polymerase I-large fragment. The promoter fragment was finally inserted into the restriction endonuclease Sma I site of pZD655 in front of GUS reporter gene to form pZD672.

Figure 4:
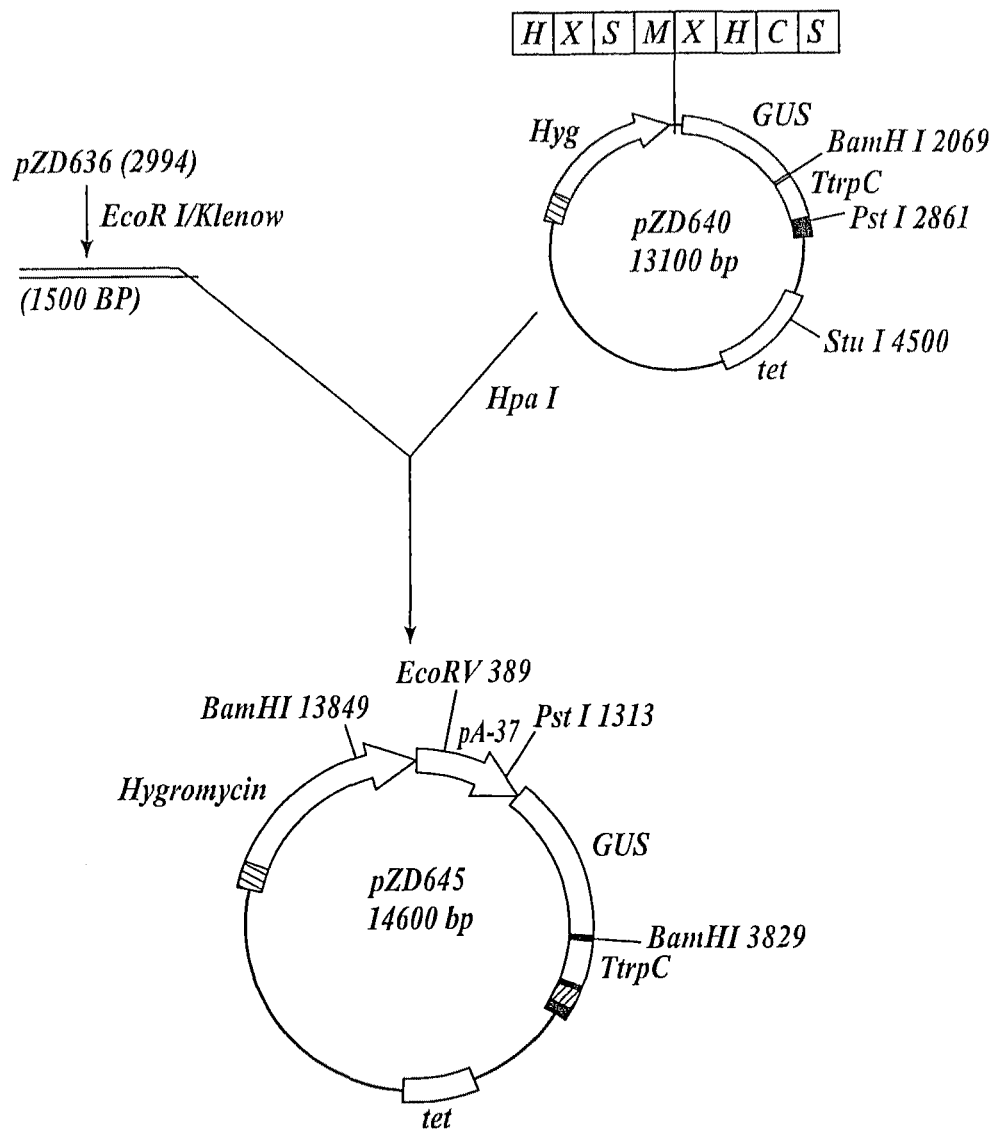
FIG. 4 is a schematic illustrating a plasmid vector pZD645, which contains the promoter region of the pelleted-associated A-37 gene (SEQ ID NO: 47) and the GUS reporter gene, for *Agrobacterium*-mediated transformation in *A. niger*.

Similarly, the pelleted-enhanced A-37 gene promoter (SEQ ID NO: 47) was first isolated from the genomic DNA using GENOMEWALKER™ kits and gene-specific primer FP-93 (SEQ ID NO: 25), which was inserted into pGEM-Teasy to form pZD612. The A-37 promoter fragment (SEQ ID NO: 47) was then prepared by PCR with primer FP-125 (SEQ ID NO: 39) and T-7 (SEQ ID NO: 45) and inserted into a PCR 4 TOPO™ vector (Invitrogen Corporation, Carlsbad, Calif.) to form pZD636. Referring to FIG. 4, the promoter fragment in pZD636 was excised with restriction endonuclease EcoR I and treated with DNA polymerase I-large fragment. Finally, the promoter fragment was inserted into pZD640 to form pZD645.

Figure 5:
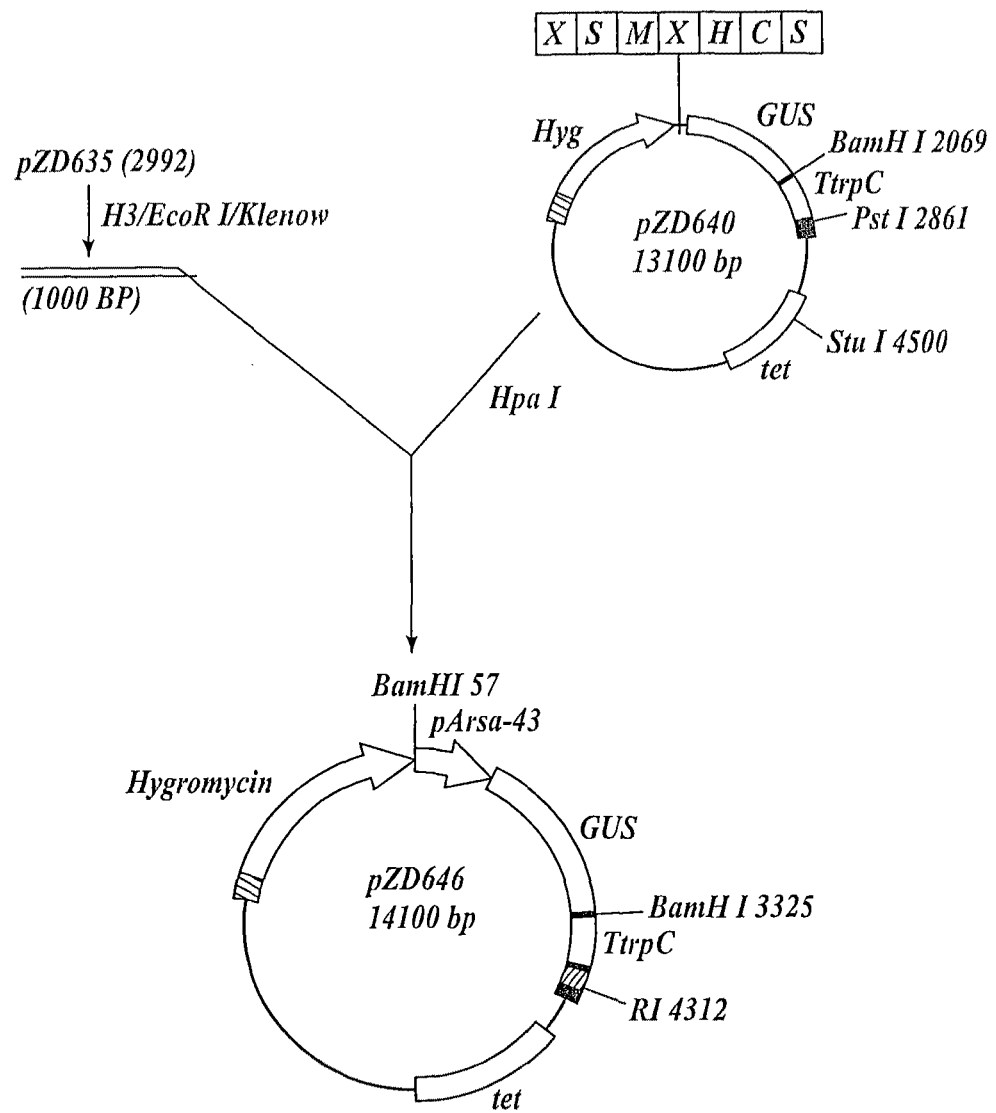
FIG. 5 is a schematic illustrating a plasmid vector pZD646, which contains the promoter region of the pelleted-associated Arsa-43 gene (SEQ ID NO: 48) and the GUS reporter gene, for *Agrobacterium*-mediated transformation in *A. niger*.

The pelleted-enhanced Arsa-43 gene promoter (SEQ ID NO: 48) was first isolated from the genomic DNA using GENOMEWALKER™ kits and gene specific primer FP-99 (SEQ ID NO: 26). The promoter was subsequently inserted into pGEM-Teasy vector to form pZD614. The ATG-sequence at the 3'-end of the Arsa-43 promoter fragment (SEQ ID NO: 48) was then removed by PCR using FP-124 (SEQ ID NO: 40) and reverse primers. Referring to FIG. 5, the remaining fragment was cloned into the PCR-4-TOPO™ vector to generate pZD635. The Arsa-43 promoter (SEQ ID NO: 48) was excised with restriction endonuclease Hind III and EcoR I, which was treated with DNA polymerase I, large fragment. Finally, the fragment was inserted in front of the GUS reporter gene at restriction endonuclease Hpa I site to form pZD646.

Figure 6:
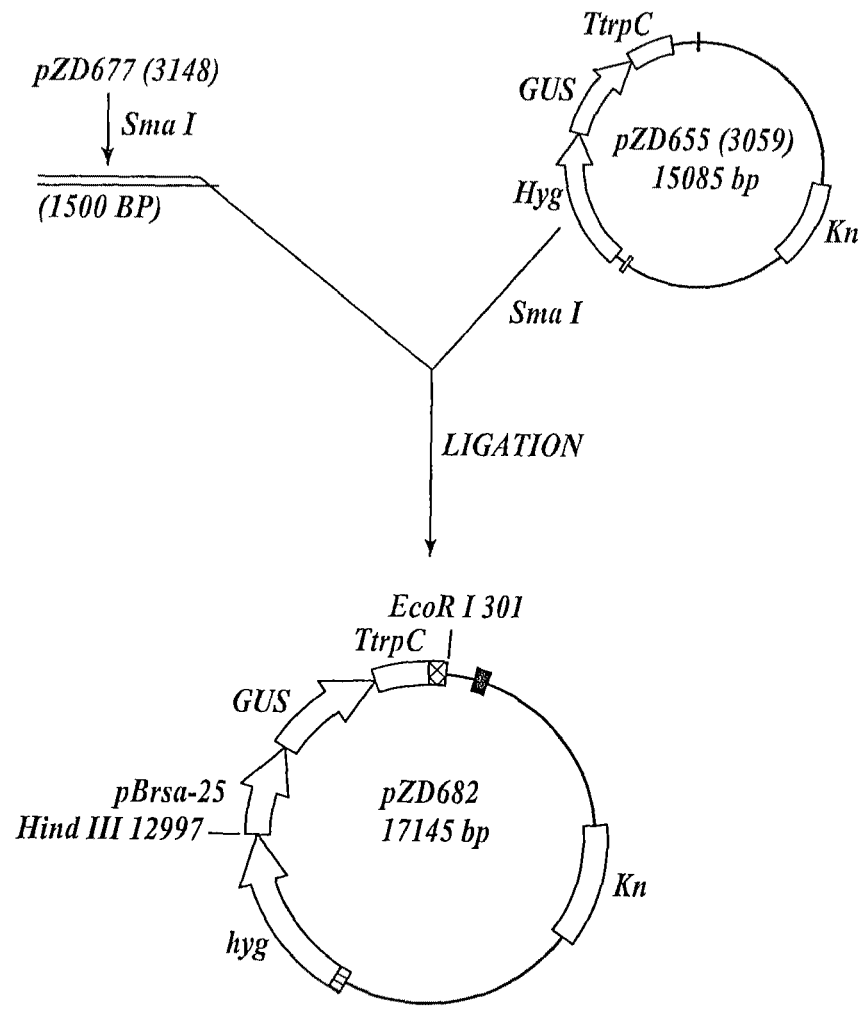
FIG. 6 is a schematic illustrating a plasmid vector pZD682, which contains the promoter region of the filamented-associated Brsa-25 gene (SEQ ID NO: 51) and the GUS reporter gene, for *Agrobacterium*-mediated transformation in *A. niger*.

The filamented-enhanced Brsa-25 gene promoter (SEQ ID NO: 51) was isolated using GENOMEWALKER™ kits and gene specific primer FP-81 (SEQ ID NO: 20). The isolated Brsa-25 promoter was then cloned into pGEM-Teasy vector to form pZD619. The promoter DNA fragment was confirmed by DNA sequencing. The ATG-sequence at the 3'-end of the promoter was removed and a restriction endonuclease site Sma I was added to the same end by PCR using gene specific primer FP-152 (SEQ ID NO: 41) and a T-7 (SEQ ID NO: 45) primer, which was further cloned into a pGEM-Teasy vector to form pZD677. Referring to FIG. 6, the promoter fragment was excised with restriction endonuclease Sma I and cloned into pZD655 to form pZD682.

Figure 7:
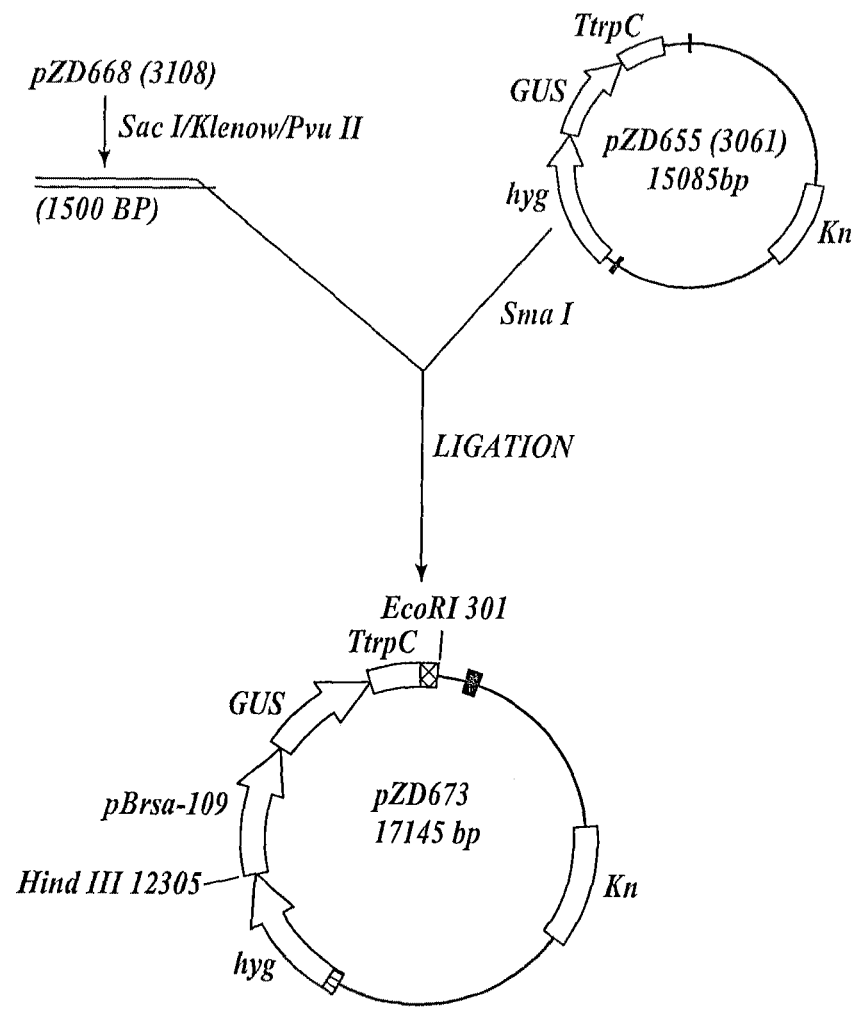
FIG. 7 is a schematic illustrating a plasmid vector pZD673, which contains the promoter region of the filamented-associated Brsa-109 gene (SEQ ID NO: 53) and the GUS reporter gene, for *Agrobacterium*-mediated transformation in *A. niger*.

The filamented-enhanced, Brsa-109 gene promoter (SEQ ID NO: 53) was isolated with GENOMEWALKER™ kits and gene specific primer FP-87 (SEQ ID NO: 22). The isolated Brsa-109 promoter was subsequently cloned into pGEM-Teasy vector to form pZD613. The ATG at the 3'-end of the promoter was removed and the restriction endonuclease Pvu II was introduced at the same end of the promoter fragment by PCR with gene specific primers FP-137 (SEQ ID NO: 42) and FP-138 (SEQ ID NO: 43). The promoter fragment was then inserted into pGEM-Teasy vector to form pZD668. Referring to FIG. 7, the promoter was isolated with Sac I and Pvu II, treated with DNA polymerase I-large fragment, and cloned into pZD655 in front of the GUS reporter gene to form pZD673.

Figure 8:
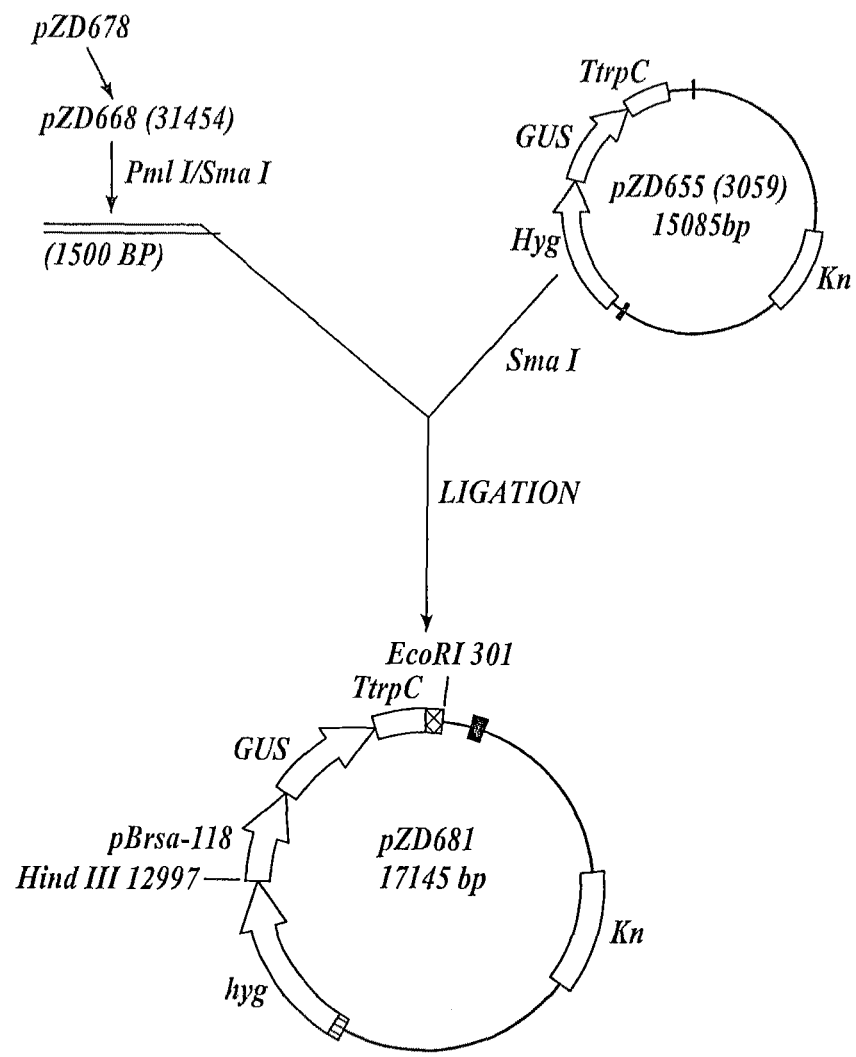
FIG. 8 is a schematic illustrating a plasmid vector pZD681, which contains the promoter region of the filamented-associated Brsa-118 gene (SEQ ID NO: 54) and the GUS reporter gene, for *Agrobacterium*-mediated transformation in *A. niger*.

The filamented-enhanced Brsa-118 gene promoter (SEQ ID NO: 54) was isolated with GENOMEWALKER™ kits and gene specific primer FP-89 (SEQ ID NO: 23). The isolated Brsa-118 promoter was subsequently cloned into a PCR-4-Blunt-TOPO™ vector to form pZD610. The ATG at the 3'-end of the promoter was removed and the restriction endonuclease Pml I was introduced at the same end of the promoter by PCR with gene specific primer FP-155 (SEQ ID NO: 44) and T-7 primer (SEQ ID NO: 45). The promoter fragment was inserted into pGEM-Teasy vector to form pZD678. Referring to FIG. 8, the promoter was isolated out with Pml I and Sma I and cloned into pZD655 in front of the GUS reporter gene to form pZD681.

EXAMPLE 3

This example describes the methodology used for *Agrobacterium*-mediated transformation and colorimetric GUS assays of the GUS reporter gene under the control of the different *A. niger* gene promoters. Application of this system enables one to study the function of the sequences inserted in front of the reporter gene in terms of transcriptional activity.

*Escherichia coli* DH5α was used as the recombinant host for routine cloning experiments. The *Agrobacterium tumefaciens* strain AGL0 served as the host for the binary vectors and in the transformation of *A. niger*.

Transformation of the constructs carrying backbone binary vector pZD640 or 655 into *Agrobacterium tumefaciens* strain AGL0 was conducted by the freeze-and-thaw method as described by Ebert et al. in the *Proceedings of the National Academy of Sciences USA*, 84:5745-5749 (1987), the content of which is incorporated herein by reference. Plasmid DNA from the transformed *Agrobacterium* clones was isolated and digested with various restriction endonucleases and analyzed in agarose gel electrophoresis to confirm transformation of each construct. Fungal spore transformation was performed as described in the article by Dai et al., titled *Identification of genes associated with morphology in Aspergillus niger by using suppression subtractive hybridization* (Applied Environmental Microbiology 70: 2474-2485 (2004)), the content of which is incorporated herein by reference. At least 30 independently transformed fungal strains were selected for each promoter construct described in Example 2. Transformed colonies were removed from the agar selective media, which contained minimal medium (see J. W. Bennett and L. L. Lasure eds., *More Gene Manipulations in Fungi*, Academic Press Inc, San Diego, pp 441-458.) with 200 µg ml$^{-1}$ hygromycin and 200 µg ml$^{-1}$ cefotaxime, and then grown under sterile but equivalent conditions for spore production. The spores were enumerated and then cultured in a proper culture medium at a temperature of 30° C. and a mixing speed of 250 rpm for 2 days. Finally, the biomass was harvested for a GUS activity assay. Fluorometric quantitation of GUS activity was performed according to Jefferson et al. in the *European Molecular Biology Organization Journal*, 6:3901-3907 (1987), the content of which is herein incorporated by reference.

Biomasses of independent transgenic fungal strains were harvested from fresh test-tube cultures by centrifugation at various times ranging between one and three days. Extraction was performed by sonicating on ice five times for ten seconds each using a lysis buffer (50 mM sodium phosphate, pH 7.0, 10 mM EDTA, 0.1% TritonX-100, 0.1% sarkosyl and 10 mM β-mercaptoethanol).

Protein concentrations were determined by the BIO-RAD™ reagent protein assay (Bio-Rad Laboratories, Hercules, Calif.) according to the Bradford method. The GUS activity assay involved incubating approximately 5-10 µg of protein in the presence of 1 mM 4-methylumbelliferyl β-D-glucuronide in 100 µl of lysis buffer at 37° C. Samples from each reaction were taken at 0, 10, 20 and 40 minutes. The enzyme reaction was quenched in 0.2 M sodium carbonate ($Na_2CO_3$). The standard curve for 4-methylumbelliferon at 50, 100, 150, 200, 250, 300, 350 and 400 nM concentrations was generated with a FL600 Fluorescent Microplate Reader. The amount of 4-methylumbelliferyl β-D-glucuronide converted to 4-methylumbelliferon (MU) by GUS enzyme was determined with FL600 Fluorescent Microplate Reader and the MU standard curve. The GUS enzyme activity is expressed as pmol MU per mg protein min.

Figure 9:
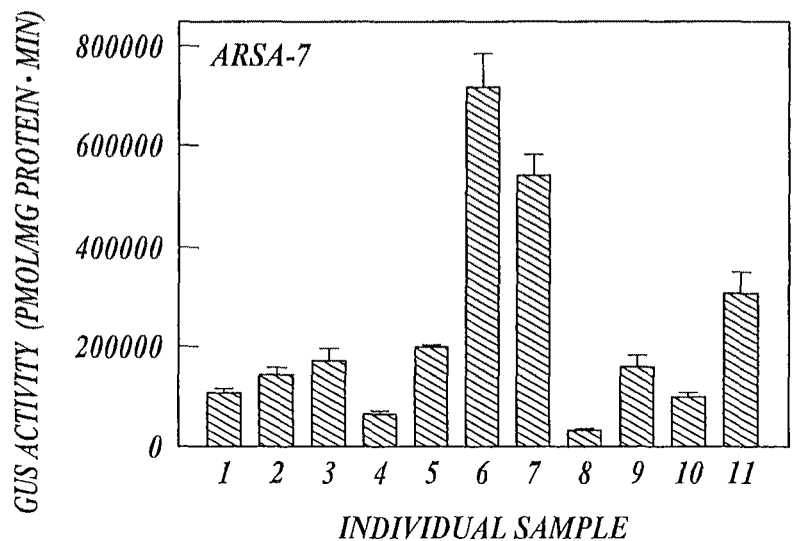
FIG. 9 is a plot of the promoter activity for a number of individual *A. niger* strains transformed with the promoter region of the pelleted-associated Arsa-7 gene (SEQ ID NO: 46) and the GUS reporter gene. The promoter activity is determined via GUS activity assays and is expressed as pmol MU/mg protein/min.

Referring to FIG. 9, the expression of the GUS gene with the Arsa-7 promoter (SEQ ID NO: 46) was at a high level and gradually increased under pelleted culture conditions. It remained at barely detectable levels for the first three days of growth in filamented culture conditions and then rapidly increased after three days of growth. The plot shows the activity of pelleted-enhanced Arsa-7 gene promoter (SEQ ID NO: 46) in the protein extract of two days old individual transformant under pelleted growth conditions. The promoter activity is expressed at pmol MU/mg protein/min. The promoter activity in most of transgenic strains is about 200,000 pmol MU/mg protein/min. Transgenic strain No. 7 has the strongest activity among the 11 strains. The promoter activity is about four times higher than the hybrid Mac promoters that consist of the B-domain of 35S cauliflower mosaic virus promoter and the manopine synthase promoter of *Agrobacterium tumefaciens*. This activity appears to be the strongest one used in plant transgene expression. It is about 20 times higher than the yeast α-amylase promoter.

Figure 10:
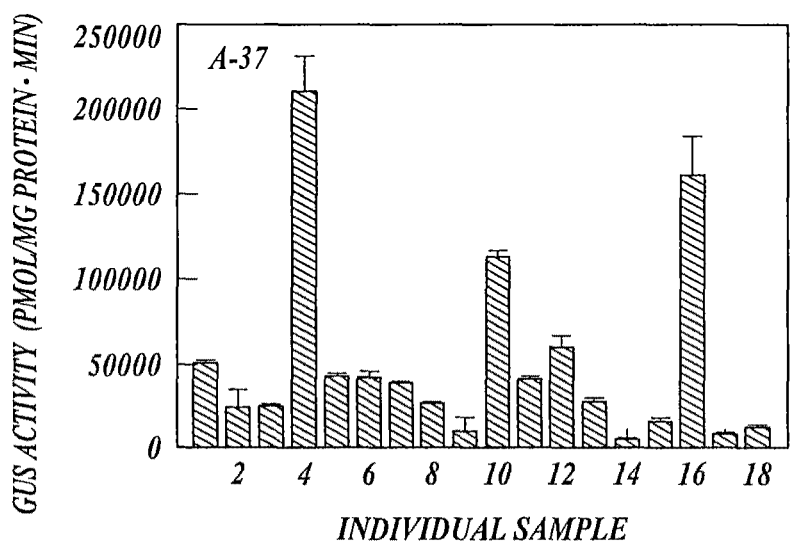
FIG. 10 is a plot of the promoter activity for a number of individual *A. niger* strains transformed with the promoter region of the pelleted-associated A-37 gene (SEQ ID NO: 47) and the GUS reporter gene. The promoter activity is determined via GUS activity assays and is expressed as pmol MU/mg protein/min.

Referring to FIG. 10, the A-37 promoter (SEQ ID NO: 47) activity is still higher than the yeast α-amylase and is comparable to that of the hybrid MAC promoter. The plot shows the activity of the pelleted enhanced A-37 gene promoter (SEQ ID NO: 47) in the protein extract of two days old individual transformant under pelleted growth conditions. The GUS activity of most transformants was around 50,000 pmol MU/mg protein/min, while transgenic strains 4 and 16 were about 150,000 to 200,000 pmol MU/mg protein/min. The data show that the A-37 promoter (SEQ ID NO: 47) has high constitutive expression levels at pelleted culture conditions. Expression was low during the first day of growth prior to the rapid increase thereafter to the end of growth.

Figure 11:
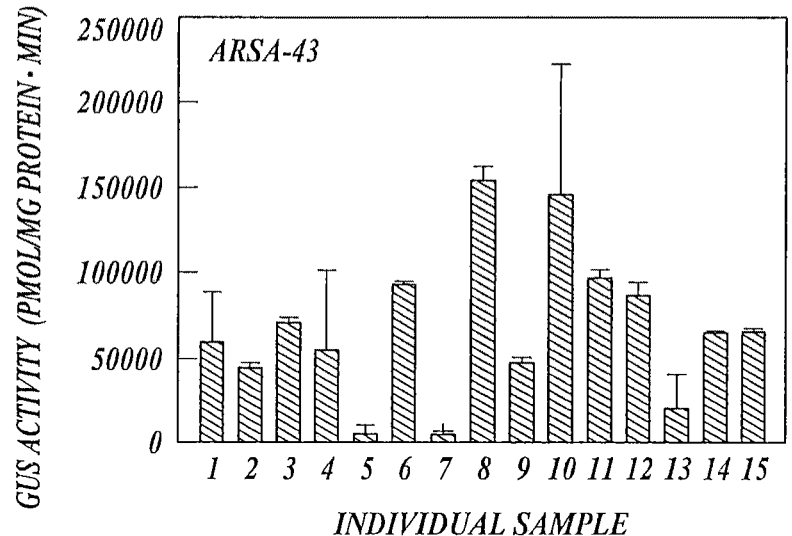
FIG. 11 is a plot of the promoter activity for a number of individual *A. niger* strains transformed with the promoter region of the pelleted-associated Arsa-43 gene (SEQ ID NO: 48) and the GUS reporter gene. The promoter activity is determined via GUS activity assays and is expressed as pmol MU/mg protein/min.

Referring to FIG. 11, the Arsa-43 promoter (SEQ ID NO: 48) is a polyubiquitin gene that is constitutively expressed at pelleted culture conditions. However, under filamented growth conditions its expression was low during the first day of growth, and thereafter increased rapidly to steady states for the rest of the filamented growth. Again, the plot shows the activity of the pelleted-enhanced Arsa-43 gene promoter (SEQ ID NO: 48) in the protein extract of two days old individual transformant under pelleted growth conditions. For comparison purposes, the GUS activity of most transformants is around 5,000 to 10,000 MU/mg protein/min.

Figure 12:
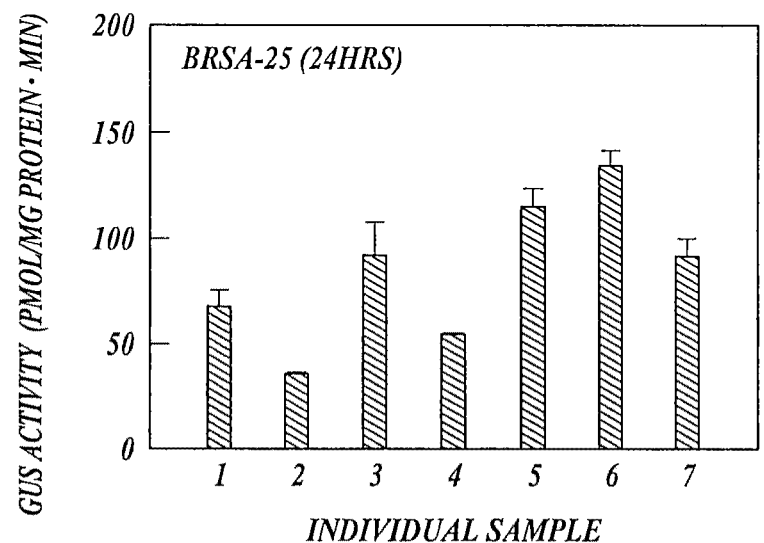
FIG. 12 is a plot of the promoter activity for a number of individual *A. niger* strains transformed with the promoter region of the filamented-associated Brsa-25 gene (SEQ ID NO: 51) and the GUS reporter gene. The promoter activity is determined via GUS activity assays and is expressed as pmol MU/mg protein/min.

FIG. 12 shows the activity of filamented associated gene Brsa-25 promoter (SEQ ID NO: 51) in the protein extract of two days old individual transformant under filamentous growth conditions. The GUS activity of most transformants is around 50 to 100 pmol MU/mg protein/min. The Brsa-25 promoter is filamented specific and functions temporally. Its transcription increases rapidly at the first day culture and decreases to low levels at two and three day cultures. Thereafter, its transcription augments to the level of first cultures.

Figure 13:
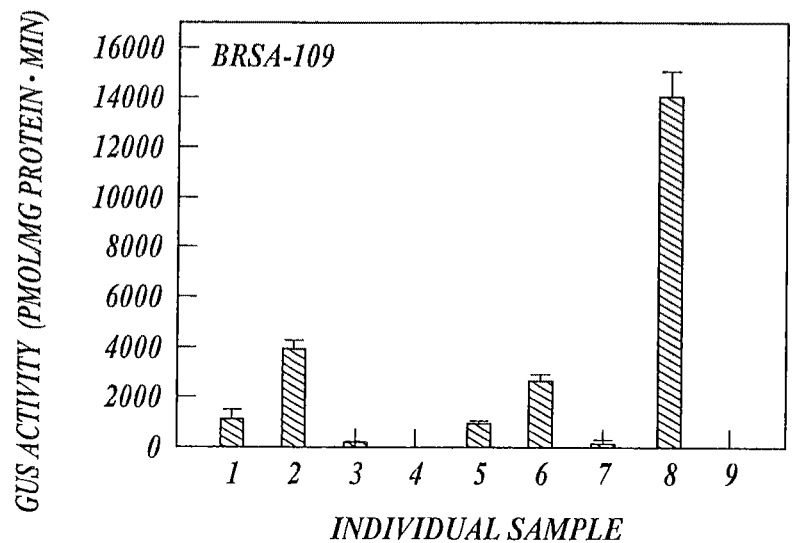
FIG. 13 is a plot of the promoter activity for a number of individual *A. niger* strains transformed with the promoter region of the filamented-associated Brsa-109 gene (SEQ ID NO: 53) and the GUS reporter gene. The promoter activity is determined via GUS activity assays and is expressed as pmol MU/mg protein/min.

Referring to FIG. 13, the Brsa-109 promoter (SEQ ID NO: 53) is constitutive and filamented-specific. The plot shows the activity of the filamented-enhanced Brsa-109 gene promoter in the protein extract of two days old individual transformant under filamentous growth conditions. The GUS activity of most of the transformants was around 1000 to 4000 pmol MU/mg protein/min, except transformant clone 8, which had an activity level over 14000 pmol MU/mg protein/min. The Brsa-109 gene promoter (SEQ ID NO: 53) can be used for the expression of genes of interest in filamented growth conditions.

Figure 14:
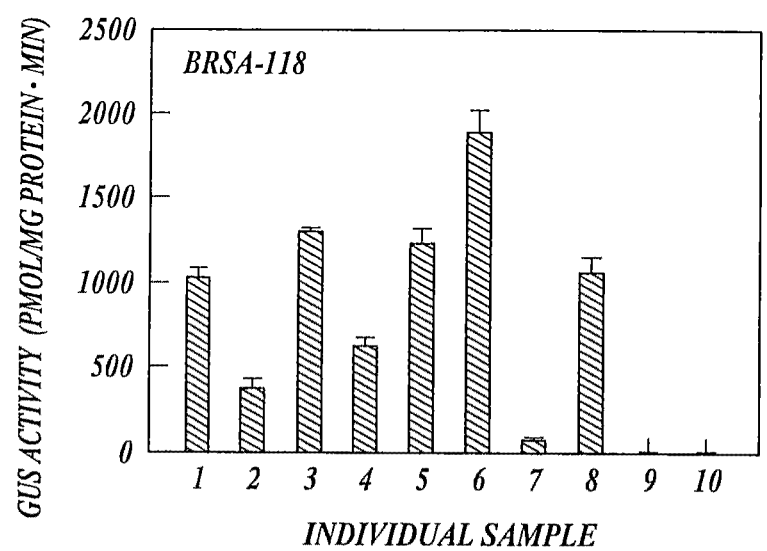
FIG. 14 is a plot of the promoter activity for a number of individual *A. niger* strains transformed with the promoter region of the filamented-associated Brsa-118 gene (SEQ ID NO: 54) and the GUS reporter gene. The promoter activity is determined via GUS activity assays and is expressed as pmol MU/mg protein/min.

Referring to FIG. 14, the Brsa-118 promoter (SEQ ID NO: 54) is temporally dependent and filamented specific, similar to the promoter of the Brsa-25 promoter (SEQ ID NO: 53). The plot shows the activity of the filamented-enhanced Brsa-118 gene promoter in the protein extract of two day old individual transformant under filamentous growth conditions. The GUS activity of most transformants was around 500 to 2000 pmol MU/mg protein/min. This promoter can be used for expression of genes of interest in different developmental stages.

EXAMPLE 4

This example describes the necessary steps taken to prepare different fungal transcription terminators and insert them into the host vector pGEM-Teasy for plasmid DNA preparation. The DNA was sequenced and aligned against known DNA fragments to confirm the newly isolated transcription terminators. The transcription terminators can be used for heterologous gene expression in fungi.

The transcription terminator of the pelleted-associated Arsa-7 gene (SEQ ID NO: 55) was isolated with GENOMEWALKER™ kits and gene specific primer FP-92 (SEQ ID NO: 31). The genome walking libraries in Example 2 were used as template DNAs for genomic PCR with adaptor primer 1 (SEQ ID NO: 35) and FP-92 primers (SEQ ID NO: 31). The DNA fragments were cloned into pGEM-Teasy vector to form pZD621. The DNA sequence of the Arsa-7 gene transcription terminator (SEQ ID NO: 55) in pZD621 was determined and aligned with the known genomic DNA sequence of the Arsa-7 gene to confirm the newly isolated fragments.

The transcription terminator of the pelleted-associated A-37 gene (SEQ ID NO: 56) was isolated with GENOMEWALKER™ kits and gene specific primer FP-94 (SEQ ID NO: 32). The genome walking libraries in Example 2 were used as template DNAs for genomic PCR with adaptor primer 2 (SEQ ID NO: 36) and FP-92 primers (SEQ ID NO: 31). The DNA fragments were cloned into pGEM-Teasy vector to form pZD622. The DNA sequence of the A-37 gene transcription terminator (SEQ ID NO: 56) in pZD622 was determined and aligned with the known genomic DNA sequence of the A-37 gene to confirm the newly isolated fragments.

The transcription terminator of the pelleted-associated Arsa-43 gene (SEQ ID NO: 57) was isolated with GENOMEWALKER™ kits and gene specific primer FP-100 (SEQ ID NO: 33). The genome walking libraries in example 2 were used as template DNAs for genomic PCR with adaptor primer 1 (SEQ ID NO: 35) and FP-100 primers (SEQ ID NO: 33). The DNA fragments were cloned into pGEM-Teasy vector to form pZD615. The DNA sequence of the Arsa-43 transcription terminator (SEQ ID NO: 57) in pZD615 was determined and aligned with the known genomic DNA sequence of the Arsa-43 gene to confirm the newly isolated fragments.

The transcription terminator of pelleted-associated A-90 gene (SEQ ID NO: 58) was isolated with GENOMEWALKER™ kits and gene specific primer FP-104 (SEQ ID NO: 34). The genome walking libraries in example 2 were used as template DNAs for genomic PCR with adaptor primer 1 (SEQ ID NO: 35) and FP-104 primers (SEQ ID NO: 34). The DNA fragments were cloned into pGEM-Teasy vectors to form pZD617. The DNA sequence of the A-90 gene transcription terminator (SEQ ID NO: 58) in pZD617 was determined and aligned with the known genomic DNA sequence of the A-90 gene to confirm the newly isolated fragments.

The transcription terminator of filamented-associated Brsa-25 gene (SEQ ID NO: 59) was isolated with GENOMEWALKER™ kits and gene specific primer FP-82 (SEQ ID NO: 28). The genome walking libraries in example 2 were used as template DNAs for genomic PCR with adaptor primer 2 (SEQ ID NO: 36) and FP-82 primers (SEQ ID NO: 28). The DNA fragments were cloned into pGEM-Teasy vectors to form pZD620. The DNA sequence of the Brsa-25 gene transcription terminator (SEQ ID NO: 59) in pZD620 was determined and aligned with the known genomic DNA sequence of the Brsa-25 gene to confirm the newly isolated fragments.

The transcription terminator of filamented-associated gene Brsa-47 (SEQ ID NO: 60) was isolated with GENOMEWALKER™ kits and gene specific primer FP-86 (SEQ ID NO: 29). The genome walking libraries in example 2 were used as template DNAs for genomic PCR with adaptor primer 1 (SEQ ID NO: 35) and FP-86 primers (SEQ ID NO: 29). The DNA fragments were cloned into pGEM-Teasy vectors to form pZD626. The DNA sequence of the Brsa-47 gene transcription terminator (SEQ ID NO: 60) in pZD626 was determined and aligned with the known genomic DNA sequence of the Brsa-47 gene to confirm the newly isolated fragments.

The transcription terminator of filamented-associated Brsa-118 gene (SEQ ID NO: 61) was isolated with GENOMEWALKER™ kits and gene specific primer FP-90 (SEQ ID NO: 30). The genome walking libraries in example 2 were used as template DNAs for genomic PCR with adaptor primer 1 (SEQ ID NO: 35) and FP-90 primers (SEQ ID NO: 30). The DNA fragments were cloned into pGEM-Teasy vectors to form pZD627. The DNA sequence of Brsa-118 gene transcription terminator (SEQ ID NO: 61) in pZD627 was determined and aligned with the known genomic DNA sequence of the Brsa-118 gene to confirm the newly isolated fragments.

While a number of embodiments of the present invention have been shown and described, it will be apparent to those skilled in the art that many changes and modifications may be made without departing from the invention in its broader aspects. The appended claims, therefore, are intended to cover all such changes and modifications as they fall within the true spirit and scope of the invention.

We claim:

1. An isolated polynucleotide molecule comprising:
    a polynucleotide sequence selected from th group consisting of SEQ ID NOs.: 47-49;
    a coding region of a foreign gene linked to the polynucleotide sequence for heterologous gene expression; and
    optionally a terminator polynucleotide sequence selected from the group consisting of SEQ ID NOs.: 56-58.

2. The isolated polynucleotide molecule as recited in claim 1, wherein expression of a native gene regulated by the polynucleotide sequence selected from the group consisting of SEQ ID NOs.: 47-49 is constitutive in a native fungus exhibiting said pellet morphology.

3. The isolated polynucleotide molecule as recited in claim 2, wherein said native fungus is *Aspergillus niger*.

4. An isolated polynucleotide molecule comprising a polynucleotide transcription terminator having any one of SEQ ID NOs.: 56-61, wherein said isolated polynucleotide molecule is combined with a molecule comprising a foreign gene for heterologous gene expression.

5. The isolated polynucleotide molecule as recited in claim 4, wherein the polynucleotide transcription terminator is isolated from *Aspergillus niger*.

6. An isolated polynucleotide molecule comprising a promoter functional in fungi, wherein said promoter comprises one of SEQ ID NOs.:47-54.

7. An isolated polynucleotide molecule comprising a transcription terminator, wherein said transcription terminator is a functional terminator comprising one of SEQ ID NOs.:56-61.

8. A DNA construct comprising the following elements operably linked in the direction of transcription:
    a. a first DNA segment comprising one of SEQ ID NOs.: 47-54;
    b. a second DNA segment comprising a sequence coding a protein of interest, the second DNA segment being heterologous relative to the functional promoter; and
    c. a third DNA segment comprising a functional transcription terminator.

9. The DNA construct as recited in claim 8, wherein said transcription terminator comprises one of SEQ ID NOs.:56-61.

10. The DNA construct as recited in claim 8, wherein said second DNA segment comprises a coding sequence that is differentially expressed in a native fungus exhibiting a pellet morphology relative to said native fungus exhibiting a filament morphology.

11. A vector comprising the DNA construct of claim 8.

12. The vector as recited in claim 11, wherein said second DNA segment comprises a coding sequence for GUS.

13. A transformed host cell comprising the DNA construct of claim 8.

14. The transformed host cell as recited in claim 13, wherein said transformed host cell constitutively expresses said second DNA segment.

15. The transformed host cell as recited in claim 13, wherein expression of said second DNA segment by said transformed host cell is temporally-regulated or spatially-regulated.

16. The transformed host cell comprising the DNA construct of claim 13, wherein said functional transcription terminator is one of SEQ ID NOs.:56-61.

17. An isolated polynucleotide molecule comprising:
    a polynucleotide sequence selected from the group consisting of SEQ ID NOs.:50-54;
    a coding region of a foreign gene linked to the polynucleotide sequence for heterologous gene expression; and
    optionally a terminator polynucleotide sequence selected from the group consisting of SEQ ID NOs.: 59-61.

18. The isolated polynucleotide molecule as recited in claim 17, wherein expression regulated by the polynucleotide sequence selected from the group consisting of SEQ ID NOs.: 50-54 initiates at a developmental stage in a native fungus exhibiting a filament morphology.

19. The isolated polynucleotide molecule as recited in claim 17, wherein expression regulated by the polynucleotide sequence selected from the group consisting of SEQ ID NOs.: 50-54 is constitutive in a native fungus exhibiting a filament morphology.

* * * * *

UNITED STATES PATENT AND TRADEMARK OFFICE
CERTIFICATE OF CORRECTION

| | | |
|---|---|---|
| PATENT NO. | : 8,735,562 B2 | Page 1 of 1 |
| APPLICATION NO. | : 12/257261 | |
| DATED | : May 27, 2014 | |
| INVENTOR(S) | : Ziyu Dai et al. | |

It is certified that error appears in the above-identified patent and that said Letters Patent is hereby corrected as shown below:

In The Specification

Column 1, line 15 – Insert --This patent is a divisional of U.S. Patent Application Serial No. 10/920,625 which was filed August 17, 2004.--

Signed and Sealed this
Eighth Day of December, 2015

Michelle K. Lee
*Director of the United States Patent and Trademark Office*

SEQUENCE LISTING

<160> NUMBER OF SEQ ID NOS: 62

<210> SEQ ID NO 1
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 1
ccacggtagt cactcctttg cacta                                              25

<210> SEQ ID NO 2
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 2
cctctattct gtctcccttc ggcgat                                             26

<210> SEQ ID NO 3
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 3
gcaatcgtct tcccgtcgtt ca                                                 22

<210> SEQ ID NO 4
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 4
gtctgtcgtg gtgtcgtatc aaatg                                              25

<210> SEQ ID NO 5
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 5
ctccttcttc cccccatac atca                                                24

<210> SEQ ID NO 6
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 6
gctgtgcttc gtaccttcat ttcg                                               24

<210> SEQ ID NO 7
<211> LENGTH: 25
<212> TYPE: DNA

```
<213> ORGANISM: Artificial Sequence
<220> FEATURE:
<223> OTHER INFORMATION: synthetic oligonucleotide

<400> SEQUENCE: 7
gccatctatc aacacgagag aaaac                                    25

<210> SEQ ID NO 8
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 8
tgcagatctt cgttaagacc ctcac                                    25

<210> SEQ ID NO 9
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 9
ctctcccacc tccccagcct ttcct                                    25

<210> SEQ ID NO 10
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 10
gagtcgacga atcgaatcga atcg                                     24

<210> SEQ ID NO 11
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 11
gacaccatca cagacatata cagaga                                   26

<210> SEQ ID NO 12
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 12
caaagagtgg ctgtagttgg ct                                       22

<210> SEQ ID NO 13
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 13
gtgcccatca gaagtgaacc aaga                                     24
```

<210> SEQ ID NO 14
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 14
gcattccagc tcctgtctgg acaa                                          24

<210> SEQ ID NO 15
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 15
cacaagcgtc caatccatca ca                                            22

<210> SEQ ID NO 16
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 16
gagatcgaca aggtaacatt ccagaa                                        26

<210> SEQ ID NO 17
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 17
gcggaggaca agatggagag tagac                                         25

<210> SEQ ID NO 18
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 18
ccaaggtaaa gcagatctaa tgg                                           23

<210> SEQ ID NO 19
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 19
actttcgtgt cttgtgcgtg aagtaa                                        26

<210> SEQ ID NO 20
<211> LENGTH: 26
<212> TYPE: DNA
<213> ORGANISM: Artificial Sequence
<220> FEATURE:
<223> OTHER INFORMATION: synthetic oligonuceotide -continued

```
<400> SEQUENCE: 20
ggtttcttta tcctgtccgt atgctg                                          26

<210> SEQ ID NO 21
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 21
gacggtttat attcgaccac gcctca                                          26

<210> SEQ ID NO 22
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 22
gctagtggcc ttcattgttg tatgag                                          26

<210> SEQ ID NO 23
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 23
tgaatgtgta aaaggaggag gggtaa                                          26

<210> SEQ ID NO 24
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 24
agtaaggcga aatgaaggta cgaagc                                          26

<210> SEQ ID NO 25
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 25
cagcagcaga cattgtgatg tgatag                                          26

<210> SEQ ID NO 26
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 26
gatgccctcc ttatcctgga tcttg                                           25

<210> SEQ ID NO 27
<211> LENGTH: 26
<212> TYPE: DNA
```

```
<213> ORGANISM: Artificial Sequence
<220> FEATURE:
<223> OTHER INFORMATION: synthetic oligonucleotide

<400> SEQUENCE: 27
gcggtcagaa gagacttgaa ggagac                                         26

<210> SEQ ID NO 28
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 28
ctgtggagta gatgggcact cttgat                                         26

<210> SEQ ID NO 29
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 29
cacccaccta gtaatgctta gccatc                                         26

<210> SEQ ID NO 30
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 30
tttgtggttc gccttaatag agcttg                                         26

<210> SEQ ID NO 31
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 31
atcatctgac gctgatgcaa tagttc                                         26

<210> SEQ ID NO 32
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 32
ggacatggac atggatatga gtttga                                         26

<210> SEQ ID NO 33
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 33
ctttagcacg gctcatctac ggttg                                          25
```

<210> SEQ ID NO 34
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 34
ttgagctcga gtggaaaggt ctacg                                        25

<210> SEQ ID NO 35
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 35
gtaatacgac tcactatagg gc                                           22

<210> SEQ ID NO 36
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 36
actatagggc acgcgtggt                                               19

<210> SEQ ID NO 37
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 37
tcaagcttct gctccaacgc gctatcaaat cgaac                             35

<210> SEQ ID NO 38
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 38
cacagctgat tgaaagaata gagagtgatg gagttg                            36

<210> SEQ ID NO 39
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 39
cggaattctc tagagtgatg tggataggga tgggaataag                        40

<210> SEQ ID NO 40
<211> LENGTH: 42
<212> TYPE: DNA
<213> ORGANISM: Artificial Sequence
<220> FEATURE:
<223> OTHER INFORMATION: synthetic oligonucleotide

```
<400> SEQUENCE: 40
ccaagcttat cgatgttgta gaagcgcagt taatggtgta tg                              42

<210> SEQ ID NO 41
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 41
atcccgggta aagcaaggcg aatgacgaag aca                                        33

<210> SEQ ID NO 42
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 42
cagagctcct cctgtctgag tgttgtctca                                            30

<210> SEQ ID NO 43
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 43
ctcagctgtt gtatgagagg tgtatatgta tgt                                        33

<210> SEQ ID NO 44
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 44
gcacgtgaat gtgtaaaagg aggaggggta                                            30

<210> SEQ ID NO 45
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 45
taatacgact cactataggg                                                       20

<210> SEQ ID NO 46
<211> LENGTH: 2043
<212> TYPE: DNA
<213> ORGANISM: Aspergillus niger

<400> SEQUENCE: 46
aaacctaatg aaaataacat gaatctcagg attatacccca tatcgactgt atcgcatcct          60
tctcattttg gcccccttga ctcgcaatca tcgggagccc acgagtccgc tgcgggacgc          120
cggctcgctc ccaatccttt gccccagggg tcaaatgagc agtcctctat gacagtggga          180
agccacgccg gtcaggccaa atattgagag tcgagagtta gttatctgat ttcgtcaagc          240
```

-continued

| | |
|---|---|
| ctgccgatcg cgcagaaact ggtagcgacc taggaccggt ggaccgccag ttaggagggg | 300 |
| actgcgaggg tgcgaagata aagtgaaaca tcccgatcgg ataaatgggc cgtgcagacg | 360 |
| ggggaccaat cagcttacgc agcccagggg atctgcatag gccacgcca gctgctccaa | 420 |
| cgcgctatca aatcgaaggc ttgaaacgaa cagatgccat aatccgacag ccgtttgttt | 480 |
| cattcagagt agctcgctag catggtgacg actggtccag gccccatttg tcgtcatctt | 540 |
| gggccattcc atccatcacc ttcaactctg ccatgcagga aaccatggat agcctagcaa | 600 |
| aaccccggca tggacagatg ccagcgaaga cttccaccct acactagggt cccctcaggg | 660 |
| tcccattcct gttaatcccc ctattattgg gtccaccttg tgagctcccc caactttgac | 720 |
| ggggaaagct ctattccgag ttcggctaca acgttcccag cgagggcatc atgtaaaacc | 780 |
| tcataaaaac gacttttttct gatggatagg cagtgcaggt agaggaatga cttccccca | 840 |
| cagtgattat catgtttgtc ctgaccatag cttgcaggat gatctgtaag cgggagagga | 900 |
| ttatgctgca cgtagaggac actgaccaca acttctgttc ctcgagatgg acccacccaa | 960 |
| ataacgtaga gtcaaggacc cgccatcgtt gggcccccaa gaacacacca gagctgacta | 1020 |
| gccttccgct tagttagcac tacgacctgt cgactgtcag tgtcgagagt cgagactggg | 1080 |
| ctgacccacc aacttggaac cgccacagcg gcaggggaca gcttgatcga ggacgtcagc | 1140 |
| tccctggcac gctggttgcc attggataga gattatcaac cagttgaatt catccaccga | 1200 |
| cgatctgagg cacttttttga ggctttccca gtgagtccac tgagtttggg tggacgatgg | 1260 |
| gtagagagac aaccagacga agcattacca agggactcat gacggaaccg caaatagacc | 1320 |
| accaacaaca gccgcagcca ggatcaagcc acctccaaga ggcagggggg ccaaggagag | 1380 |
| ggacagtcga gtcatctatt ctgaataggc gatgaagaga tgaaacgctg gagtgtcggc | 1440 |
| tggcctgtga ctgcttccag ggcgagccgc gcacgtgggg ccgccacaga cagccagcca | 1500 |
| gacttcttcc cttctcttcc tatccatcaa tagcatcctc tacctacata ctcccttctc | 1560 |
| acagatccaa ctaccggctt catgcttagc cgacccacag aagcccagca ggtacgttca | 1620 |
| aaccctattt tgcatcagcc ctgccctga gccactctac cacccccac aagcgccggg | 1680 |
| tctgccgatc cgtgcggttc ttgcatgtcc agcataacct gatctattgc tgacagtcga | 1740 |
| cgtctcagat gcaggcgagc cgaattcggt gacaacagtg catgacgaat gcttggttct | 1800 |
| ttccacgcat ctcaccagat ggatggaggt catcatcgct gggtcactgc cgacccagcg | 1860 |
| cttggagagc gccttataaa agcctccctt gccccagcca ggatcattcc tcattcagct | 1920 |
| caaattctct ttcctttgat ctcaactacc attccttaag aagctgtgct tcgtaccttc | 1980 |
| atttcgcctt acttttttttc tgcttactac tacaactcca tcactctcta ttctttcaat | 2040 |
| atg | 2043 |

<210> SEQ ID NO 47
<211> LENGTH: 1565
<212> TYPE: DNA
<213> ORGANISM: Aspergillus niger

<400> SEQUENCE: 47

| | |
|---|---|
| ctgacgttga cattgaacgc tccatcaacc aaggagttgg gggtatcgag tttcatccct | 60 |
| atggggccaa acaattagca atgcttaatg cttgtgcaga aaataagcac accgggaatg | 120 |
| cgaggaaccg acagcctgca ttaaactgtg cttcggaaat tttatttccc tcctctgaga | 180 |
| cagtctcatt gatccttctg aaaatttatc cgatgggatt tccacagcac gctgtgctgc | 240 |
| ctatcgtgga tgctcgcacg gaagtttcta tatcctgatc gttaagcagg atcatgttct | 300 |

```
atatttatca ctcatggctg agctgctctt agacatatca accgcactaa aatggcgatc    360
agagcaacaa ttaacaatgc cgaggatatc gatttgtcgc ctgattttg agtaagtttg    420
tctatttta ctcggtgaaa cagcgtctca gccaggaacc gttacgagta cgacacagcc    480
aacacgggcc ataacaaggc gagcccctga tcctcgggc ccccgtcgtt cacgagccga    540
ggtgatcgct aagcgggact cgcggatcaa caggcgcgac cgtgtttcag atgtcaccat    600
gacaaggtgg ctatgagtaa ttccaggcga cgtgccgtgt gttagtgcca tgcggcaatg    660
atgggccgcc aagagtagtt ggggatgcag tggagagaga gagagacaac tcatacccag    720
atttgattca ttacttcagt acgtgcagac atgacatctg ataaaaccta ttccgaccga    780
gtcgtggttc tagaccggcg ggcttggcga ccgcaacacg acctttgcgt acattccaga    840
cgacgaaaca ctgcatcagg cacgggcatg ccggatcgag cgagacccct gacagaattt    900
ggggcggccc ctgatgatgt gcggcctcaa agcgtcatca cccatttcaa cctgccagga    960
acagcaacgt tggagccaat cgcggatgca aatctggctg cctagaatag caattgccac   1020
ggcctcagcc cccgtgattg cgcggcccaa caggccttcc attggctgaa accccggata   1080
agccttgggt tttgtgcagt agtggaagct tggcaagtta ctgagccaat catattcctc   1140
taattcctcc aaggagggtg ggggcctgct aacgtcacgg acctgcttcc attgccttcc   1200
cctctgcccg tccttccatc ccagcccggt cggccgcgtc acagacccgg ctggaaaggc   1260
aacaaggctc gcaacctcat gcccatcatt ggctggtcct gcgtgatgct gcaggtcagc   1320
ttccaaactc agtcgcccat gctgaccttt ttttatgcag ccgggctgct tctttcattt   1380
ataggtcccc gtctggcatg tgtcttccct tccaacttcc cgactcactc cacctttct    1440
catctgtcat ctgtacctag attccttctt atatcttatc cgtggttcct tctttctgg    1500
ccaagatctt agccatctat caacacgaga gaaaacttat tccatcccct atccacatca   1560
caatg                                                               1565

<210> SEQ ID NO 48
<211> LENGTH: 982
<212> TYPE: DNA
<213> ORGANISM: Aspergillus niger

<400> SEQUENCE: 48
ctggagagga tccccttccc ccatcttccg ataagggatg cccccaactc acacgtcatc     60
gccgttgctg ccgccgcaag gccagttgtc gcattactcc ctgatcacca ccagtttgcc    120
tggtgagagg atacgaacaa ttatgagcaa ttcttcggag tagcaacgag tattttcacc    180
gggagtttca acgggttcta tttcaggaac acggctgcgg tctggattgg gtcgggctga    240
gataccgact ggtggcgtca gtggcgggta cggacggagt cgtcctggcc gctcgtagac    300
actcccccgg actgatatca ggccccggca actggcttcg tctcactcca gggcatcagg    360
agtgcctacc acatgggttc aggctttgcc ccgtcgtcta agtttgcagg acaaaatttt    420
cgtatgcgtt accactcttt cctttcagca accattccgt agtgaaaacc caataatagg    480
tggctgccgt gggagcctga gtcaacccaa ccagaacctt tctagtagat tctcccccaa    540
gcgcttcagc aacgaagcgt attggagaac caaatgacgc agaccaagcg gattccggtg    600
caatagccgg atgcaaggg aatcccccag gaggtgccag aagcgtcgcc cgaaaggtac    660
ttcgtctgac aggctaacac cgctcgggct aaggtccctg ctgctctttt cccttttattg    720
cgacttaacc tctaagccat tcccttgcat cacgttatct cactgaccga cctctgacta    780
aggcgcttcg cctccgccgc ctccccctcat tcacctcctc tcctgactgc ttaagccttc    840
```

| | |
|---|---|
| tcttccttcc tctcactacc aaccctcctt catccctcat acctctcatc ctaccactca | 900 |
| cctttcgcgc atcgccatct gcgatcctcc ccacaacact ccacctagat acatacacca | 960 |
| ttaactgcgc ttctacaaca tg | 982 |

<210> SEQ ID NO 49
<211> LENGTH: 748
<212> TYPE: DNA
<213> ORGANISM: Aspergillus niger

<400> SEQUENCE: 49

| | |
|---|---|
| atacacctcc attaaagtag ggggaataag tcggatacat ccactggacc gatcaactgc | 60 |
| aggtatccgc accgctgcag gaacaaccac cgcaaggtta cccccggacg cttgctgtcc | 120 |
| agtcactgcc aaccgccagg cacacgggct gaataatggg cgtcaatatt tctctgtccc | 180 |
| actgtccctg agcgacacac ggtacccgcc cgatgacgtt ccatgggtcg ccgcggtga | 240 |
| ggatgcaggg gggtcaggaa cgctccgacg caggcaatca gaggggtcc gccgaacaat | 300 |
| ggaaaagca acgattagtg actagttcga ctatactcat gcaagagcaa aaagaaccct | 360 |
| tcctcttgtg gagacctgat tggtcggaac caaattggcg cctagaaaaa gcacccagcc | 420 |
| ctaacttggt tctgcaactg ccactccccg ttgttgggcg tctatataac cgccctcttt | 480 |
| cccctccctg tctcctcttc gaaactcttc ttcctcgcct agatcttcct ctcccacctc | 540 |
| cccagccttt ccttctttgc acctgtgccg tgcacggtcg agccattcct ccattctttg | 600 |
| aacatattgc ctggctccga gtagtctagc atccactcct tgcaagagca ctttgagaga | 660 |
| accggtcttc tcatactcaa aagttataca tacacatcac ttctctccga acaaaaccga | 720 |
| acagaattcg aagaacacat acacaatg | 748 |

<210> SEQ ID NO 50
<211> LENGTH: 2271
<212> TYPE: DNA
<213> ORGANISM: Aspergillus niger

<400> SEQUENCE: 50

| | |
|---|---|
| atccacagca gatggatcat aagcagtcag actgcaggtc aggtatcgga gtccgagaca | 60 |
| ttcgaactag tctccgacgc cactggaaaa attcctgcac tcgcccacac gtggtaagcg | 120 |
| atacgactac atattgtgtg gacagaggaa tgtggcctcg agcagagaaa gcttgccaac | 180 |
| atgaagatca ctggcaggcg tgctcatgaa agccattccg tgggttttgt ttggataacc | 240 |
| cgcaaggtac atactccggg agtgcttgtc tcttcaaggt tcgcagtatg acggatcatc | 300 |
| tcccttggta cgaaggaagg catgttatca gttatcgtgc cttgttagtg gcattggcag | 360 |
| tcggaacgag ggtccactaa cccagtcagg aacgaggaat gagcgacagg aaccagagaa | 420 |
| tcttcaccca acatagcgat ggatgatctc atcgaggacg ttgatcacct ctctcgcggg | 480 |
| gactttcaac gacgaacggt cagtttgcag aatgaaaccc ccttgacaat ctgttgatct | 540 |
| gcggccagtg gaagaaagg agggagtacg tgggtagtaa catgacttgt gtgtttcttg | 600 |
| gtgtctctcc gtagcaattt aggcgaccat ccgattacac ggggtggag acaccggaca | 660 |
| ggttccttgg tgcctttgga ggacacgaga tgcgtttagt gcctctggtc ccaatattcg | 720 |
| gaaggtggta attaaactct gtgcctggcc acttcggtga tttaacgctt cggcctcgtg | 780 |
| gcgtgtctat gtctcatttg tgtcaaacca ggacgcaccg gaagcagctg gcaaggctcc | 840 |
| ggaaggcgaa gccaatcaag caccactcga tgagggcac tgatccatcc attgtaaatt | 900 |
| ttacatgagg gtaatttccc aggtaatttg ccctgcgggct atgtcattga gaatggaaaa | 960 |

```
gtctccggat aatatttgcc aaaaatgtga gatgtgtgtg cgtgtgtgaa aacgctcgag    1020
cttctggaag tgaaacaaaa gctgaaagga aggaggtgg tgatggcgat aatggtggtg     1080
gtggtggtgg tgtttgtttg tttgtttgcg cgcgaatccc ttgcgggcca agttccacca    1140
acgacttctc tttctactgt gtctcttcgt actccgtcca gctgctgcta gccatcaaca    1200
acatccttcc ttctccgttc tcggggttcc tccgttgttc ctggcctggt ctgacataag    1260
gttatgattg tttcacatgt cccacggctt cgccggcttg gagctgagac cctcttctga    1320
gtcaatggta ccattttgcc gaattcgtgg ctagttctct atttctatgc tcttgacttt    1380
ggtaccgttg gcattagttt gatctactaa taaagagcct agttttaggc gaatatacac    1440
tgttacccac cgggtagtat tcagtagcta ccctcccact ccccaggctc ccacgctgag    1500
agccttgatt cgatgtctct cctaaaattg ctaggctgtt agcgccctgg cagatgaacc    1560
cccgctcatc cctcgtatat gcggtctcaa tttctgagtg gcccacgcct ccgagtatct    1620
ttgagcacat ccacgatgga gggaggcgat ccaagcggtc taacagcgga ctaaaccgct    1680
ctgtgtaagc cagtcagaga gtcatactgg cttgaggtga catcgccaat tcatttcaca    1740
aggtttagtc gggggagggt aggccccata cattccaccg ttctcaaagt ttaccaggca    1800
tttctcacac taaccatgca atagtaggta actagcagta gtcttgaacg ctgttcctga    1860
gcaagttccc aatcagcaat ttgaaagaat aatttccttt gacccaccgg gtaaatgagc    1920
cgcagatttg gcgatgttgg gctcggagcc tggtaggtag tagtgaatgt catcccctcc    1980 ataggggga attgggaggg gggctgtgaa tggacttgtc ctacgcctgt cgcatcccca    2040
tcattcatat acttgaatgt ctcttctccc ccctcctcct tctctttctc tccttcsctt    2100
ctcacgattt gacgtccctc gcgttttcgc cctctcccac ggtagtcact cctttgcact    2160
acatacacga agtcttactt ccagtcactc tttgaaacca cttctcaata tccctacctc    2220
ttatcattct ttacttcacg cacaagacac gaaagtgaac ctgtaaaaat g             2271
```

<210> SEQ ID NO 51
<211> LENGTH: 1680
<212> TYPE: DNA
<213> ORGANISM: Aspergillus niger

<400> SEQUENCE: 51

```
atcctgaggt tgccaccatc aagtgcttgg tctgtttcca aggtacacat attctgcgta     60
gtggactaga acatccactt actacgtcgt tggagccgat gcggaggcca agcttcgtgc    120
ttgggaaaca agcaacaggc caagcaacga gtggatgggg cttggagcca ctgagcggtc    180
atgccgtcca tgggactggc ctcgatagta gaaggtcctt ctgataagcc cgtgtgcaca    240
gggcctcccg ggtttccggc tagtccatgc acacaggtttt tcttcactcc tttccctcac    300
ccctggccac ccatctgagg ttcatccaat cggtgacccc cgagaatgtc tccgcgctac    360
catagtagta tctagcactc ttagctactc ataagcgaca agtcttttttg ggtttcgtgc    420 cgctatggct ggaaccatta attccggacg taggagcgtt gcagtcaggt agattgttgt    480
gtaagggaaa ttggtccatg aaaatcggca aaattgatgg gaagcaagac aagggagcgc    540
tagtgcagcg gtcgcatggt cacggttccc ccatccactc ggttctccgt cggcaatttc    600
tgtctttcct ttcccttttg tcgttccctt cactttattg gggttattta ttgattctgg    660
taataatatt cgctcttatc ttcccccaac cgtcacgaaa atgggccttg gtccgatgtg    720
tgtgcatcca caaccgacca cccacaccac tacctcgtcc tcctccttcc ctataggcca    780
acattgcctt acggtgtatc ggacggtgct ccagatcgaa atttgcgatc caataagtcc    840
```

-continued

| | | |
|---|---|---|
| cctgcagaca ctaatcaagg tcaggtctca ttgggcgcga taacgtgctt cggccaggca | 900 |
| atcacactca tgaccatatt cttgctcatc ctcatcctca tccacatcat atcatcagga | 960 |
| tttcagtaag gtcagcagca tccgactcca gccgcagcaa gcctgtgacc ctggtctagt | 1020 |
| ctgcaattct ccgaacaaac gagcgtgttg acggtggagt ctcctggttc gtggcaagcc | 1080 |
| gttcgtgcag cccacggtta tctggtgtgt taccctccta aatcagttaa ccaagacgcc | 1140 |
| accoctcctt cggaccttcg acagatgctc cagaagacct cgatgtgcca atcaagttcc | 1200 |
| tgactagcgg tgatggcctc ctcaaagtgg ggagatgcag accgtttaag tttccactgg | 1260 |
| accgtcaatg gcattctgaa tgggtgccca ccgtggctcg aacatcgctg ctactggcgt | 1320 |
| tgattaaatt gcatcgataa ccagtgctgg atcagctcat actgacggcg ataatgtaga | 1380 |
| tactagccca cagtaatcca tcggattccg cctgctaatt ccgctcctcc cattcccatt | 1440 |
| tgtccctttg gttattagct agtggacgtt atctcccccg tcagcctccc attgactggt | 1500 |
| ctggcaccca ctaccagcta ctctgtagtc tcgcgccccc gtcgcgtgct tgctgcttgg | 1560 |
| cccttcttaa gcaccgccga tcccacctcc cccagttctg gatctttgca cccctcaagt | 1620 |
| tcgtcctcta ttctgtctcc cttcggcgat tgtcttcgtc attcgccttg ctttaccatg | 1680 |

<210> SEQ ID NO 52
<211> LENGTH: 2344
<212> TYPE: DNA
<213> ORGANISM: Aspergillus niger

<400> SEQUENCE: 52

| | | |
|---|---|---|
| taatacgact cactataggg cacgcgtggt cgacggcccg ggctggtctg gcagatatat | 60 |
| gtttagaaac tgtccgaatt tcgagaacag acggccggtc acacagagac gtcgtaatcc | 120 |
| ctcgactgcc ctcacgcatc ctggtggacc gattgtccgg gtgacgcaga tcgaaacctt | 180 |
| ctgctgattc ttagctgtgt agcgtccagg aaccggtgac ctccgtacca tggctcggtt | 240 |
| tcaatagtac ccggcagtcg gcgacgcgca ttgctctcaa gattgagtag gatacctaag | 300 |
| gattgtaaac catgatgaca ttcttttgtgc gtagtcgagg ttcaatctca tgatctggcg | 360 |
| gacgacaggc catgggtacc tgcctacgga ctatgcacga ctgctgtctt gtgtccgatt | 420 |
| ggcggacaat atccctcccc tagcagtact ctgtagtgcc gcagtgtgca gtaatgtact | 480 |
| ggtgtaatgc tccacgcaag ctctggatac ataccactat atcctaaacg caaaaccttt | 540 |
| gaatagaacc acttcttttg gatgatggat cccacatggt ctgactatat attctgctgc | 600 |
| gcgtcaagcg gctatctcac tgtctgacac tgagtcgctc gtcgtcagcc catggcgttt | 660 |
| gagtcggtta gttttgcttg ccgaaggtct agccgagtct ctgcccgaat gtttcccgcc | 720 |
| ctccgccaat cccacggccg atggacagcc tcaggctgcc ttccagccca tggatgccgt | 780 |
| gttgcctgag gaccttgcag cgggcgctat cacatgattg tgtcacagca agcaatgagg | 840 |
| agcagatcat gattagtgta cttagcttga accctactac taaattgcac acagtcattg | 900 |
| gaacaccaca cacagtgcaa tggtggggac aagcgccaaa tagactcgtc tcctttttcac | 960 |
| aatccaggca gcagtcctgt tgggccgttg tgcacgcatt accgatggaa tagtccaggg | 1020 |
| gtcgtgatcc taccacggct cgtctgccga gctctccgct gctcccctgc ccacacacca | 1080 |
| cgagcttcct gtcgagcttg cttgcccgtg gcaattctga ttcgttctga tgcattatat | 1140 |
| ctcatgacta ttcttctcct atgaagtagc ctcctggcat atattctgca atattaactg | 1200 |
| gcacaagtct cgcttcagtc tggtgtcagc gtcggcaatc aactcctcat tatcgcgatt | 1260 |
| cgcgggcgga gccccgcgac tccgactgcc tgctagtaac cgacccacca tcgatgatgg | 1320 |

```
atggagccca ggccacattc cgtcccgggc caggggggtc cggtgccagt ccttgagttc    1380
aactgtcttc gtcccatctt taggacaccg ctgctgggct tcttcctggg gataatcatg    1440
gcacccatga ttctatctcg ccgttcgtgg gctagcggca ggccaatgcc gggaacggca    1500
cagcgggcct ttatcgagac actgccaggc tatggcagag ttgtatagcg gaatggccat    1560
tttgagctgg aaggaataga ttcaaggtac tcgagagtca caatccgtaa gccacattca    1620
ctccgtatca ttatctagcc tctcattcac cagtcaaact catgagtgtc cggtagacat    1680
aggcacgatc tgctcaccgc aattgtcatt tgtgggatgt gctggacata cttggccatt    1740
tacgctttta cgcgggcgct cggaagtcaa cacctcgcta gacaatccct gaagcctgtc    1800
atttgccagg aaggtggact agtgcactgt tgagctggtt gggggtgcgg agcagtttgg    1860
atccggatac ggtcagcaac gtgacccgcc gtataagtac cgctcccctcc tcgctttccc    1920 tcgacccttc ctccttctac cacccatcaa taccttcagt tcgttagcaa tcgtcttccc    1980
gtcgttcaat tcaacttctg atcacactct ctgaggcgtg gtcgaatata aaccgtcaaa    2040 atttttcgcca cacttcttaa ctcgtaagtt ccccaccatt ctccgcggtc tcccgacgat    2100 ggctgccccct atcccagtgc tccaggaaca gcaattggac cttcctccaa gcaatcccac    2160
tttccagggt cttcttatgg ctaatctgtc tcctttcctt taggcggcac cacccgttca    2220
acggccggcg ctcatccaac cgtggtgggg caccggacta cgcattatac gtccagtaaa    2280
caactcgcag tctgaacact cgtattatct gtctcgcacc ccaatctgtc aactgtgaac    2340
aatg    2344

<210> SEQ ID NO 53
<211> LENGTH: 1838
<212> TYPE: DNA
<213> ORGANISM: Aspergillus niger

<400> SEQUENCE: 53
cctcgatccc actctcccca ccctcctcct gtctgagtgt tgtctcatat acctcacccc      60
cagcgaagcc agcttggtag tccgccactt cacagaaacc atctttccgg cgaccacgcc     120
ggtagggttg gttctgtatg agcccatccg gccagacgat gcgttcgggc gcacgatggt     180
ggcgaatcta gccacgaggg ggattcagtt gcagacattg caggagtatg cgtcgctggg     240
ggcgcagcga cggaggttac gggagatggg attggacggg gggcaggcgg cagcagatgt     300
agatttcatc tgggaaaggt gggtgagtga gcgggagaag gaacgggtgg cagggttgga     360
gatgttggat gagatggagg agtggcagtt attggcaaga cattattgtg ttgcatgggg     420
gtggagggat gttcctggtg gagtgtttga gggatggagg gagatggaag ggcaggagga     480
gtaagagtat agtaagtata gtagtagtgt gcgtcatacg tgatggctag ctagctagtt     540
agtttgttgt acctaagtag ttccctagac tatcatataa ttattatata tgaatgaaaa     600
tccacgttga acgcttcgga gcgcacaggc caaggggcga aaagaggag aagaagtgga      660 atcctgatgg aaaaaatggc agtccaagca acgtgcatgc aaccacctca ggacccctgt     720
ctattgaatt attattattg acaattattg cctgatttca tggtactcga cagggtataa     780
tggcagtttg cctagcaatc atttcattcg tgcaatcaaa cctgacggta gatacgagcg     840
aacgagcaag cgagagacag actaaacata gactattgcc taagctagca ctgtagctcc     900
ccgcctctgt gtacaattgg cttgcgtctc ccccttttttc aaactgccaa agtccgtgcc     960
ggtcagtgac tgagactagc tcagaggcag aggcactgac tcgattgaac tcgagcacta    1020
ctttctggct tatactggaa taggatgctg atccggtctg gacgtgtgct gatcgtgatg    1080
```

```
tcttgactgg gagaggaagg gagtggttga gagtttgtcc cgtgtcatat ttcgtagagt   1140
tgagttgact tgacagcagg caataattat agatttgagc tggataagat ttaacagaaa   1200
tttctgtata ctctctatcc cccctctctg tgtctatact gtatcctttg cgtgagtgat   1260
cccaccaagt atggaagagt gtctcaaagg gtccacggac cccttatcca tccatcagga   1320
acagtacggt aacctacact attccactat ccccaaagaa gtaatctacg ggggtattc    1380 catgaactgc cgcagtgcaa aggccgctga ttggcgtgac cccctgagcg ggtcatgcct   1440
gattgggatc gaagctttaa ggctatccac attgggtaac ccggggagag catcactttc   1500
aggctactag cagtagacta gtagtcttct ctagtcctgc tggctggtgg ttgtgggttt   1560
ctcttttctc ttgtcttttc cctcgttctt ctctctttct tctcttcttt ctttctctgc   1620
ttcggtccag tctctcgttc ttgtctttac tgacccctagt cttcgtttc gcgtggtctg    1680 tcgtggtgtc gtatcaaatg attattatta tcttctaacc tatccctctg cctatttgct   1740
atatatcccc aaaactgacc catacatatc acatctctcc acctttggtt acatatacat   1800
acattcatac atacatatac acctctcata caacaatg                          1838
```

<210> SEQ ID NO 54
<211> LENGTH: 1506
<212> TYPE: DNA
<213> ORGANISM: Aspergillus niger

<400> SEQUENCE: 54

```
ctgataactc ttgcctggcc attacgacga tccttcgtcc attcgagtga gtaactgagc    60
catggtggaa gggaaaagtg tggaaagagg gagaagacga ggggcatgcg acactcaaag   120
cctacggatc gggcaagacc atcagacaag cctatctatc ctgtgtggtc tattagatat   180
gccatctgat ccgaaacaat aacccgtaaa aagatactcc gagtccagac ggagttttcc   240
tcgcaagcag gtttgtcgtc atgggcaatc aatggccggg acgcagggga gagacaaagg   300
ataccaggga acgcatccca ttgccgtgtt aaagtgcttg gcatcccggg gacagagggg   360
tacattgcgg gtttacatca tgtgtctgca gttaagctgg attgtgtaag tagggtaata   420
ttattgcagc agtgagctcc aaaaagtacg gtggtgtgga gattgaatcc tcacgttcat   480
atcggtcagt gtgggagagt aacatgggcc gatgttgatc gagggcgggt gtatagttag   540
ggtgaatgcc atatcacaga acatggcggc aagagccggt gaaaaggaaa aggcaaaaaa   600
gaatcatcca cccggagcaa gatgagctgt cggtaagacc acttggagct aggttgtgca   660
atgatgcgtt gggtgtgaga gctgtggttg gaggcagccg tatcctgctc ccccgttttc   720
gggacatagg atgaagagta cggcgtatac cagatcctgg acaccatcag attttctccc   780
tctcaacaat tgtggaaatt aggaggtgga tcgttctgag ttgggagtcc tgtccggtga   840
aacttcccat ccacaatttc gaccccttttt cttctccccg tcatggggga gaaatggtgt   900
atcgtcgaaa gaagtttgtt gatatgatgc gccgtgactt cgatcaccca aagaccatct   960
atactataga tctgaggcgg cgtgactgcg agaacaccgg cgggacaacc tcaggcaccc   1020
cagggcaggc cagggcgccg accaaccaca gcttgcagac tgagccagac aggcccacca   1080
ggccacgcac tagaagcaca ctaaaaaagt agctgatccg taagtattgt ctggctgcat   1140
aggaacgggg gccgacccag ttcgttgctt tttttttttc ttttttttctt ttgcctccgg   1200 ccgatggtca gtgaccacct gggaaaccgt tcgcccgctg gtctcggggg ggatcctcta   1260
gtatatcgtg agcttcacta cttatactct cctcttttcac cttctctcaa gctccttttt   1320
tctttctctc tcctccaaca aatttttctc ctcttacttt taatcatttt cttttattct   1380
```

-continued

| | |
|---|---|
| ccttcttccc ccccatacat catactctcc gcaatagctc tctttcttga gtgttttgtg | 1440 |
| tcttaaactc tactgtccca ctttccgctt aatacttacc cctcctcctt ttacacattc | 1500 |
| accatg | 1506 |

<210> SEQ ID NO 55
<211> LENGTH: 1171
<212> TYPE: DNA
<213> ORGANISM: Aspergillus niger

<400> SEQUENCE: 55

| | |
|---|---|
| tagtccaccg aggacatcga caatgccatt gtgtcggcgt ggaccagaac aacaacaact | 60 |
| ggatgaaggt gtgatggatt ggacgcttgt gtacattaat cactcaataa ccagtcattc | 120 |
| ctttgaccag atctggtaga aagacagaat tcggctgaaa ccttctctga atgtagtcca | 180 |
| tcgcgtagca ctattatgtc ccacttgctc taccatcatc gctaattctt gggattgatc | 240 |
| gtctcacttc cccatggaat atatactacc tggctcattt gatgagcccc actcctgttc | 300 |
| ttgatatata ccatgtaact tccaaattct gacggcgtag attctcctag actatttgaa | 360 |
| gtaaaataat agccatatgc tcacaaatcc aggcaacaat atcagatcat ggcaatagca | 420 |
| tcattcaggc tgatgtatta cgccaattag tagtggtagt agtagtagta gtagtagtag | 480 |
| tagtagtagt agtagtagta gcacgcatct tcaatatcaa aataaataag ctcattcttt | 540 |
| ttggtgtcca ctataaagcg atagtactgt atcgaacctc caacacagat ctatagcacg | 600 |
| acctccccgc gattgaaaat atatacatga cacaccagtc atgaccccaa gtaaaatacc | 660 |
| actgctcgca gtaggaacta atcttccctt acctgccccc catctactcc ttccacgcgc | 720 |
| acatcatgac tactaatatc cccctcagac cccaaatcac tctcacttct ctcaacttcc | 780 |
| atcccctcac cctgaaccac tttcggcctg cacggaaaac aatcaatcag catatcccac | 840 |
| taaccccccat cccccccgagc aagcagaata ccaacatacc ttttctcccc ctcccaaatc | 900 |
| tgcaacctcc acgtcgccac cgtcgaaata atcaaaatca cagacataat cgtcaccgta | 960 |
| ataaacccctt ccggtactgc ggtgcatcca cctgctgcca caccaccagc ggcaaccagg | 1020 |
| cttgaaacac gtacgccatt tcgttcatgc tgcccacgac tagcgcgcgc tcttcgttgt | 1080 |
| catcggtgca gatctcgtgg gcccatcttt acattttatt aggttagttt cgggggatgg | 1140 |
| agggatggga tgggggagg gggttggcac c | 1171 |

<210> SEQ ID NO 56
<211> LENGTH: 878
<212> TYPE: DNA
<213> ORGANISM: Aspergillus niger

<400> SEQUENCE: 56

| | |
|---|---|
| taagatgaga cttggcgtgt gaatatactg cgaatgatgt tcgatttctt gtgattatgt | 60 |
| ttgggttcgg cgctggacga cgtatggata tggacatgga catggatatg agtttgatttt | 120 |
| gattgagcgt gtacattact tcactgggta tgcttctgga atgttacctt gtcgatctct | 180 |
| tatttcatac tcctccatct ggggtttacc gacacccggt attcccaatc aaaactaact | 240 |
| gcagttcaca ccgatcgaca ctactgaatt gcatcgcacc tcgttccaag gatatcctcg | 300 |
| cttccagaga aacaaactac gccctcgcag ctctaacctc tcttggcacg cccgtattga | 360 |
| ctggccgacc agcaggcgaa ggcttggccg tatatatact ttatccggtc ctcggcctcc | 420 |
| gacccactgc ttgcctctat ccggatataa gcatccactt caccaagacg ctatccgcca | 480 |
| ctacagcatg ctttgggata atgtcccact caattgccac tcctactcac cgtataggtc | 540 |

```
ttcttcgctt ggctgaagat ataagtttcc aggcaactat acttggctga tcttggcatg      600
ttcgaggaag atggaagggg catagttac ggggttactg agtaacgggt ggaaaggagg       660
gagaattggg ttgttgttta aatgtctggt gggagccggg gggtgttgaa gttggaattt      720
gatcgttata gtcgcccgtt tgatactagt cgctctttta tacgttcact ttgtttgttg     780
gctaccatga agctgtctct ggctgttggg gcagccctga tgggatctgc tctggcagtg    840
gatattgatc ccatcgtcat caaggtagac cagctcag                             878
```

<210> SEQ ID NO 57
<211> LENGTH: 1150
<212> TYPE: DNA
<213> ORGANISM: Aspergillus niger

<400> SEQUENCE: 57

```
taatgcctta ttttgatctt tcttctttag cacggctcat ctacggttga gtggcctgca     60
tggcgttggg acggttgttt tcatcggttt ttatgatacg gataaattgg gcatacctta    120
gggtcaccat cttccatggt gccttgcgtc attcttttac ctaggaatca attcaataat    180
catattccac ctgatatcta ccgctttttt tttgtagatt tagtaggaac ttgaggtaga    240
ccgttacacg ctttcagaga cgccgtcaac gtgcagttca agtcgctatc aaccaccta    300 cataacaaca tgagacgata tcaaatagga actgaatagc ttcaacttca tctacctgta    360
aattatcgaa caagtaacag acatcgagcg tgagtcaccg tcttcgccac ccgtatctcg    420
gcacgtgact gataccgtcc caaggcggcg tgggacagga agtagcttc cattcatgaa     480 gctgacccag gagagcagtt gcaggcctgt agcacgctgg agatgtgagc atcagtcgtg    540
atgccctcct acttctacca cattgcgatc gaattatttg ctcgcccgca ctctgacctc    600
caaggcacat acccaggcgt ggacaagcac tcgacgtcgc tatctttcga ctccgcatgc    660
gaatctctac tcccgttcca gaagcgccgg cactcaccgt gggcacatcg atcttctcgt    720
catcaagcgc atgggaaaca cccacgcccc tcacccaaca ctttcgccga aacccacggc    780
tcagactcta caaccagcgt tgcggacctc cgtaccctc acctctacac gacttcgccg     840
acaagcgcat ccgacttcga gcgcgacctc aggcttgata aagtatccat cgagtgcatt    900
gacatgatcc catcggagca ggacacaact gctgcgaagc ggacgggctg aagaatgca     960 aaggagaatc ccatcgcgac cgggatcggc acggatatct ggggaggact acgcacgaaa   1020
ggcaaataca taccgctaga ccagagtacg tcggagagtg tttggggaat cgtgcatctt   1080
taccgagatg ctcaggagac gccgttcttg acagaagagg actacccctc gtacttgaaa   1140
ggttcggcag                                                           1150
```

<210> SEQ ID NO 58
<211> LENGTH: 938
<212> TYPE: DNA
<213> ORGANISM: Aspergillus niger

<400> SEQUENCE: 58

```
tagaacaacc aactaccttt ggattccatt agatctgctt taccttggac ttttatcccg      60
tgataccttt ttgtgctgtt ttttattcta ttccattcta ccatccatct ctcacctaag     120
agggaaagag agacggacaa ccccattttta cccacccact ttactttcca atatattaca    180
attccaattt gaatcaaatt caaatccaaa tctaaattaa attaaattaa acacaacaca    240
tcacaaactt cctacacaaa aattgtaata atcaaatcat aaatcacatt caccaaacct    300
gaccctctcc acaagtccac atactaatct ttcccccta aacacactat tgggccccgt    360
```

-continued

```
tccacggatc ccccgaccca gaaagcagca acattggtcc ttgctcctcc ttaccccgtt    420
gacttctaca tatccatgga caacacacag cacctgccgt gttcattggc cggaaggcta    480
tttttgggtt tccatcgtct ggttttgttc atgttgatta tcatggagat ttaccgggtt    540
gggtttggtc tgggctcgct tggctgcggg tttcttttt cttttctt ttttcgtgag       600 gagttgagga cgtgttttaa gtaatttctt gattgagagt gagagagata agtactagtg    660
gggttcggct tggttccaat ggctcggtaa attgggcctt cgtcagtgag tgactctacg    720
tagtagataa tgtagagtct ggagagtctg attttttcc tcgcgtttct tggctggctt     780
ggcttgtgta acgtcagtt gactagtact ttttgttgtt tcttgcttgg ggttgttaga     840
cgaggtctag atagaagtag agattcagag gtaaaagact gttaagcggg tatgtatcat    900
gacaggtgtt taggttaggt aggtagtagt cggtggat                            938

<210> SEQ ID NO 59
<211> LENGTH: 423
<212> TYPE: DNA
<213> ORGANISM: Aspergillus niger

<400> SEQUENCE: 59
tagaggggag attaaaggag agtgcactgt ggagtagatg ggcactcttg atgaaactgt     60
ctataatatt attgttagta gatggtgatg atggtatata tgctctcatc tctgtatatg    120
tctgtgatgg tgtcattatc atgtatggta cgacatggat gtgattttaa tgttaatgct    180
atgatcttct atcattattt ctaaatccac ttatatcctg tgtctacgtt atcaaccgtt    240
ctccactcat ttcccctctt atttgccact accggcttct tgccattcca cttgctgaat    300
cgccctagcc cgcgcttgag cagagccagc actgacatca ttgctctgta cagaggcctg    360 ccccccagtca tcctcgaacc gaatatccgc cacagtctta gccgcatcat ccacctcaac    420
cag                                                                  423

<210> SEQ ID NO 60
<211> LENGTH: 635
<212> TYPE: DNA
<213> ORGANISM: Aspergillus niger

<400> SEQUENCE: 60
tagacaccca cctagtaatg cttagccatc atgctaggcg ttgatcacac tttacccatt     60
gtcagccaac tacagccact ctttgaatat cagtgactac cattcgtatc accattcttc    120
tcatatctct ctcattgtat atcactatca cttcgtatac cacacatccg tagatatcta    180
tgcgtcttcc ccaaatccga ataagcattc aacgccaact gccctcccaa atgcgcaaac    240
agaatattcc cctgaatctc ccccctcttg accaaatcca tcatccccgc aaaactcttc    300
ccctcataca ccggatccgt aataaacgcc tccgcttcgc cgcaaactca atcgcctccc    360
acgtcctctt atccggcact ccatacacac ccccatgcca ctcctcccac aactccacat    420
cctcctccga tacctcctcc ctccccaacc caatcctctc cgccgtctcc ttcgcaatcc    480
gcaacacctg ctccctcgtc tcctttccgt ggcactcgca tcaatcccca ccaccctcgt    540
cttccccctc ccatttccag cctctcgatc caacttctcc aacaacttac cagcccgggc    600
cgtcgaccac gcgtgcccta tagtgagtcg tatta                               635

<210> SEQ ID NO 61
<211> LENGTH: 800
<212> TYPE: DNA
<213> ORGANISM: Aspergillus niger
```

<400> SEQUENCE: 61

```
tgaattatga gcatatgatg gacttgcttt cgaccttgct tctttggaca tgaccggttg      60
cttagacggt ttaactagat tcccttcagc atgcgcattg tttatttgtg gttcgcctta     120
atagagcttg ggggcagcgg aatgctccta ccaatttccg ggtctgcttt tctccttac     180
attggttctt aatgtttcat acgttgttca tgtatcctcc tagggaggag accttctctt     240
gtccagacag gagctggaat gcaattatat aagacgatga ccaataattc cagactcatc     300
aagagtcaga agaagagtc atgaaaggac aatgattata atatggctaa tcaagatgta     360
taacttgaat aactgtctgt agtctttctc tgttttctcg accggattgt tggttgctta     420
ctgtagcata ccttgtcatg tgacatgggt gcaaagagtg gcgtgttctt cctgcacctt     480
caccccgttg caagttgcac tggttgaccc aagcgcctaa gtgacaggaa atggatagg     540
tagacatcct gctaggttca gggacttatc ggtgggcgtg aaaccaggca tgaccaagaa     600
tagcagcagt ttgagctaca aggacgctct attgttttac ttcacgccga ctccgtttag     660
agtatctgtc agtctctgtc tgacccatct acagccaaac ctcgtcacac aataagcact     720
caagttcatc taagatgact gtgattggtc cagaccagcc cgggccgtcg accacgcgtg     780
ccctatagtg agacgtatta                                                 800
```

<210> SEQ ID NO 62
<211> LENGTH: 1775
<212> TYPE: DNA
<213> ORGANISM: Aspergillus kawachii

<400> SEQUENCE: 62

```
ctgcagccag cgggaggaaa aaagggaggg actacgtggg tagtagtagt agtagtagta      60
acctgacttt tttgtgtttc tccgtagcaa tttaggcgac tatccgatta cacggggtg     120
gggacaccgg acaggttcct tggtgccttt tggactttag gagaggacac gagatggatt     180
gggtgcctct ggtcccaata ttcggaagtg gtaattaaac tctgtgcctg tccacttcgg     240
tgattaacgc ttcggcctcg tggcgtgtct atgtctcatt tgtgccagac caggactgac     300
cggaagaagc tggcaaggct ccggaaggcg aagccaatca agcaccactt tatgagggc     360
actgatccat ccatcgtaaa atttacatga gggtaatttc ccaggtaatt tgccctgcgg     420
gctatgtcat tgagaatgga aaagtctccg gatattattt gccagaaatg tgagatgtgt     480
gagaggggaa aaaaaaaaa aaaaaaacg ctcgagcttc tggaagtgaa acaaagctgg     540
aaggaggaag gagagggacg agcagacgag gaaaggaggt aaatgatggt gtttgtttgt     600
tttgcgcgaa tcccttgcgg gccaagttcc accaacaaac ttctctttct aactcttttt     660
cccttccatc acaacaacat cctcccttct ccgttctcgg ggttcctccg ttgttcctga     720
cttggtctga cataaggtta tgattgtttc acttgtccca cggcttcgcc ggcttagagc     780
tgagaccctc ttctgagtca aatggtacca ttttgccgat atcgtggcta gttctcttac     840
ttttacgctc tggattatgg taccgttggc attagtttga tctattccgt actaataaca     900
agcctagttt taggcggata tacactgtta cccacaggta gcattcagta aatacctcct     960
cccactactc ttaggctccc acgctcagag ccttgattcg atgtctctcc taaaattgcc    1020
aggctgttag cgcccctggca gatgaacccc cgctcatccc tcgtatctgc ggtctcaatt    1080
tatctcaatt tctgagtggc ccacgcctcc cgagtatctt tgagcatatc cacgatggag    1140
gggagcgatc caagcggact aacagcggac taaaccgccg tgtaagccag tcagagagtc    1200
atactggctt gaggtgacat cgcctattca tttcgcaagg tttagtcggg gaagggtagg    1260
```

-continued

```
ccccatacat tccaccgttc tcaaagttta ccagacatct cttagactaa ccatgcaata    1320
gtaggtaact agcagtagtc ttgaacgctg ttcctgagca agttcccaat cagcaatttg    1380
aatgaaagaa taatttccct tgacccaccg ggaaatgagc cgcagatttg gcgatgttgg    1440
gcttggagcc tggtaggttg tagtgaatgt catcccctcc atagggggga attgagagag    1500
gggggctgtg aagggacttg tcctacgcct gtcacatccc catcattcat atacttgaat    1560
gttcctttcc cccccctcct ccttctcttt ctctcgttcc cttctcacga tttgacgtcc    1620
ctcgcatttt cgccctctcc cacggtagtc actcctttgc actacataca cgaagtttta    1680
cttccagtca ctctttgaat tacactctcc aatatcccta cctactatca ttctttacat    1740
cacacacaag acacgaaagt gaaatcgaaa aaatg                               1775
```